(12) United States Patent
Solomon et al.

(10) Patent No.: US 6,585,873 B1
(45) Date of Patent: Jul. 1, 2003

(54) POLYMER GELS AND METHODS FOR THEIR PREPARATION

(75) Inventors: David Henry Solomon, Officer (AU); Greg GuangHua Qiao, Brunswick West (AU); Georgia Patras, Ascot Vale (AU)

(73) Assignee: University of Melbourne, Parkville (AU)

( * ) Notice: Subject to any disclaimer, the term of this patent is extended or adjusted under 35 U.S.C. 154(b) by 0 days.

(21) Appl. No.: 09/532,654

(22) Filed: Mar. 22, 2000

(30) Foreign Application Priority Data

Mar. 23, 1999 (AU) ............................................. PP9392

(51) Int. Cl.$^7$ .................... G01N 27/447; C08F 26/06
(52) U.S. Cl. .................. 204/469; 204/470; 526/261; 526/258; 526/286; 526/288; 526/301; 526/302; 526/303.1; 526/304; 526/305; 526/306; 526/307.3; 526/307.4; 526/307.5; 526/307.7
(58) Field of Search ................................ 526/261, 258, 526/286, 288, 301, 302, 303.1, 304, 305, 306, 307.3, 307.4, 307.5, 307.7; 524/548, 555, 559; 204/456, 469, 470

(56) References Cited

U.S. PATENT DOCUMENTS 3,607,292 A    9/1971    Cerwonka (List continued on next page.)

FOREIGN PATENT DOCUMENTS

DE    45492Y/26    6/1977

(List continued on next page.)

*Primary Examiner*—Jill Warden
*Assistant Examiner*—Alex Noguerola

(74) *Attorney, Agent, or Firm*—Baker & McKenzie

(57) ABSTRACT

A crosslinked hydrophilic gel in which the crosslinker used in a compound of Formula I or Formula II

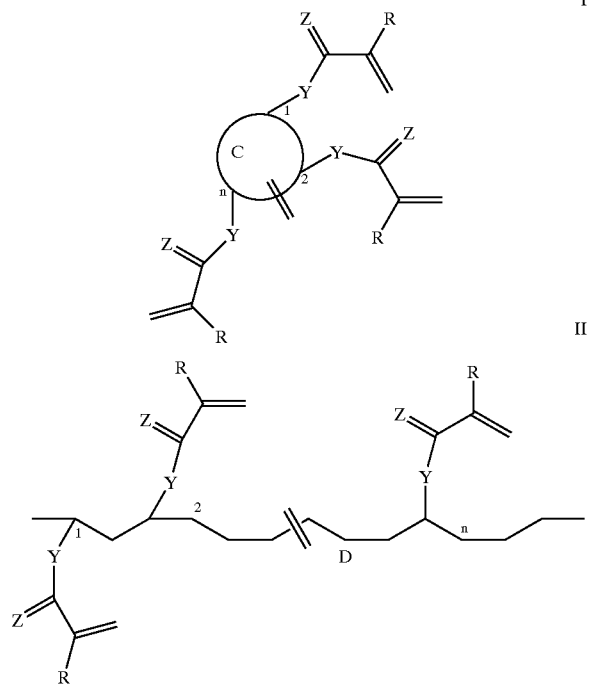

or combination thereof. These crosslinked hydrophilic gels provide enhanced separation in electrophoresis. The use of the crosslinkers of Formula I and/or II can result in electrophoresis gels having improved properties including:

1) a broader pore size range;
2) control of pore size distribution;
3) greater resistance to hydrolysis in alkaline media;
4) greater clarity of gels prepared with high concentration of the crosslinkers; and
5) improved background silver staining.

35 Claims, 10 Drawing Sheets

U.S. PATENT DOCUMENTS

| | | | |
|---|---|---|---|
| 3,801,638 A | | 4/1974 | Cerwonka |
| 3,822,089 A | * | 7/1974 | Wichterle .................. 254/2.1 |
| 3,957,742 A | * | 5/1976 | Kveton ....................... 526/261 |
| 4,612,118 A | * | 9/1986 | Kamiyama et al. ......... 210/490 |
| 4,695,354 A | | 9/1987 | Sugihara et al. |
| 5,837,789 A | | 11/1998 | Stockhausen et al. |

FOREIGN PATENT DOCUMENTS

| | | |
|---|---|---|
| DE | 4207465 | 9/1993 |
| EP | 0 165 069 A2 | 12/1984 |
| EP | 0 168 233 A2 | 1/1986 |
| JP | 11094796 A | 4/1999 |
| WO | WO 97/35896 | 10/1997 |

* cited by examiner

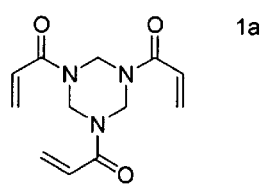 1a
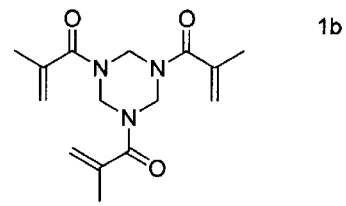 1b
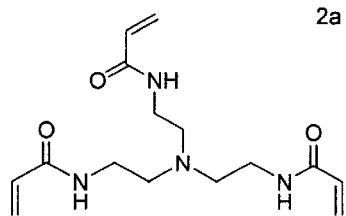 2a
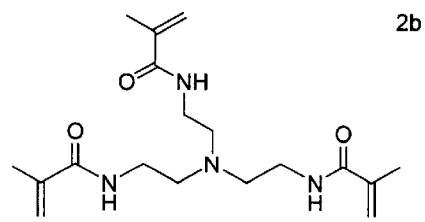 2b
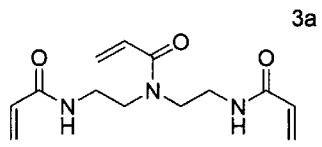 3a
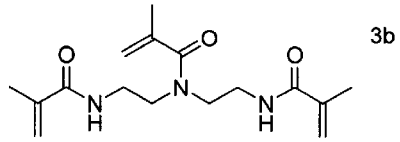 3b
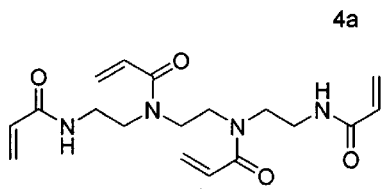 4a
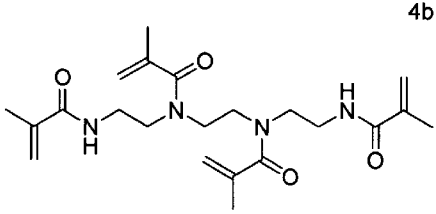 4b
Figure 1: Diagram of the new crosslinkers and their abbreviations

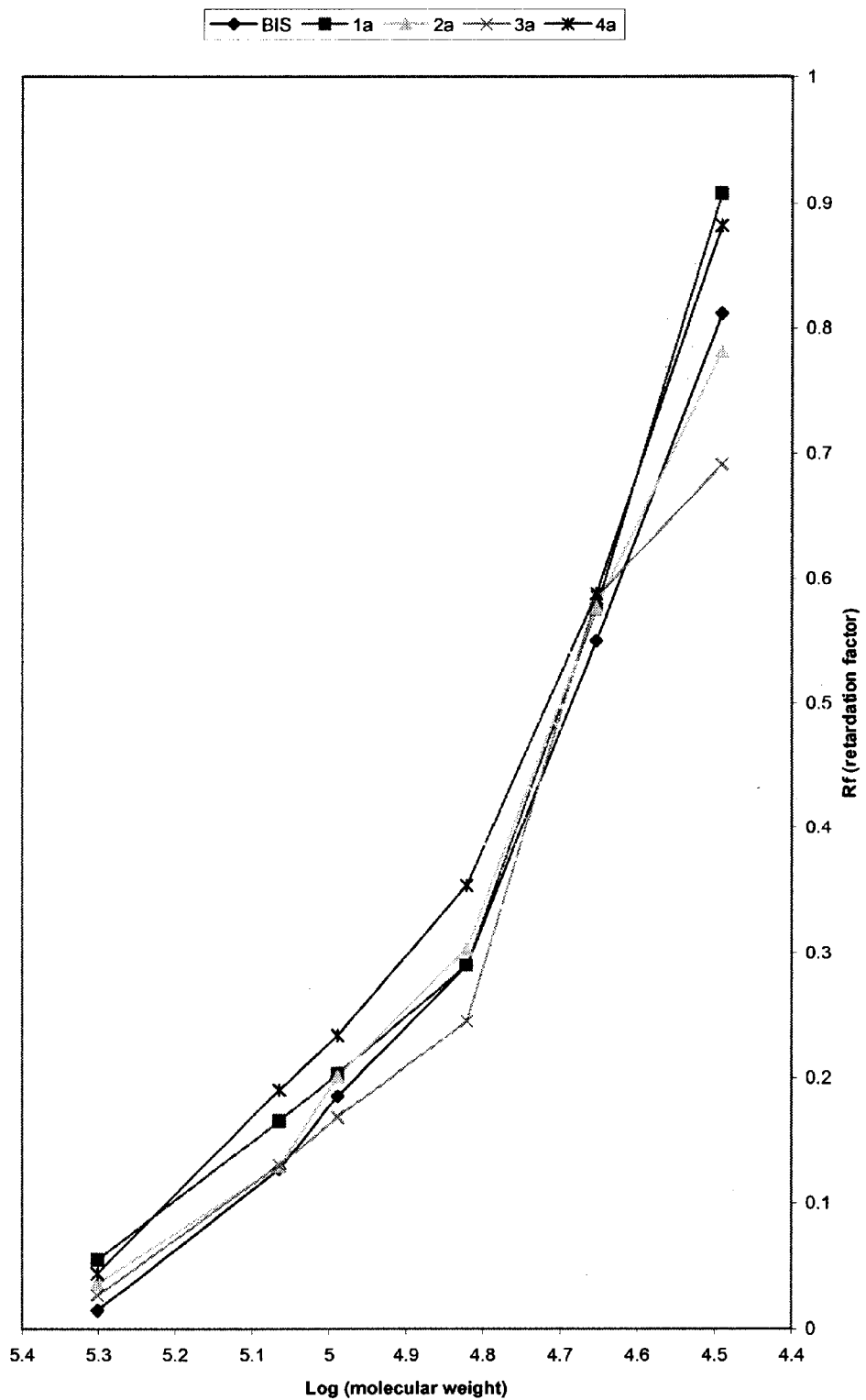
Figure 2a: A graph of the Rf values plotted against the log of the molecular weight of the proteins separated on polyacrylamide gels crosslinked with BIS, 1a, 2a, 3a and 4a.

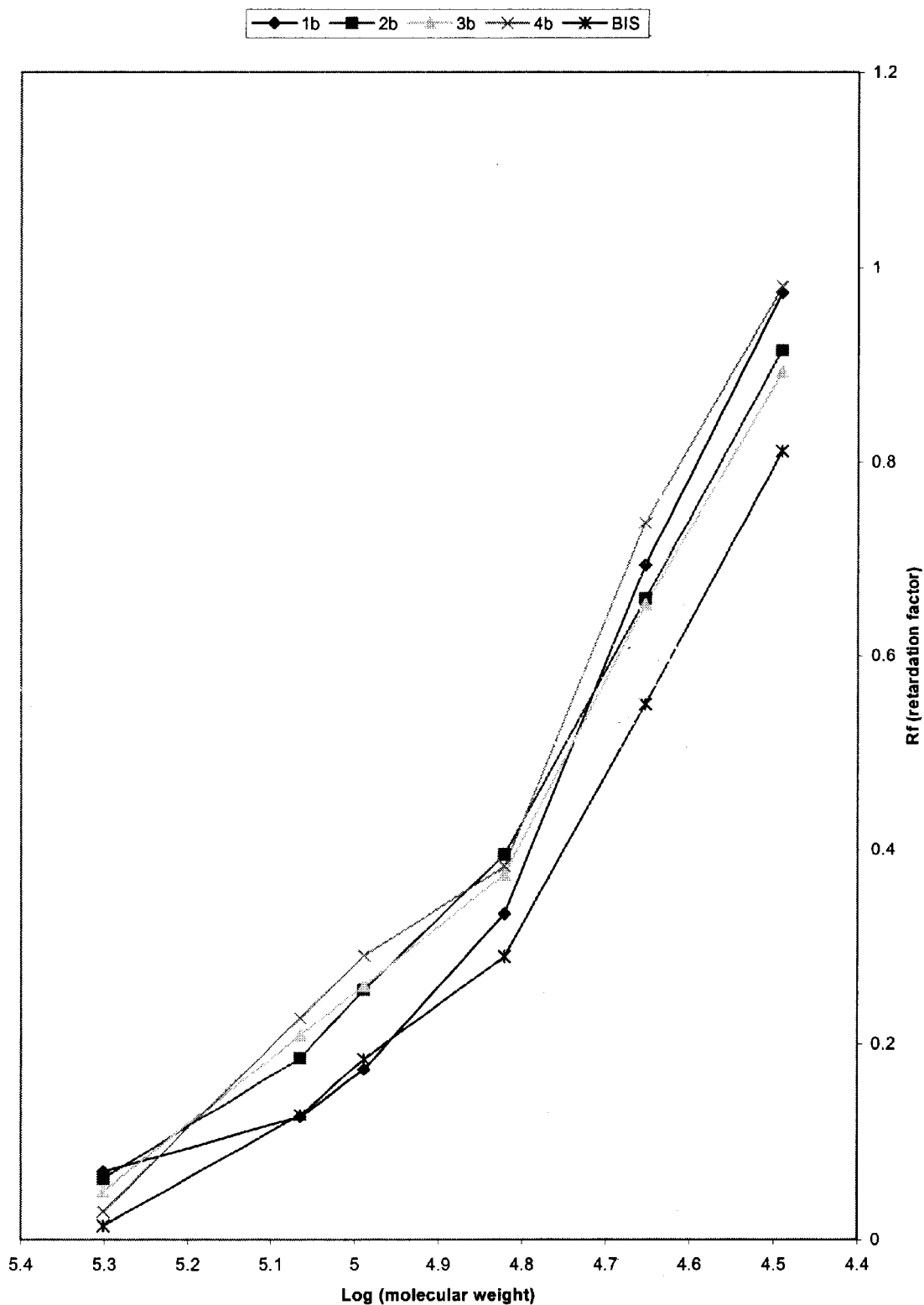
Figure 2b: : A graph of the Rf values plotted against the log of the molecular weight of the proteins separated on polyacrylamide gels crosslinked with BIS, 1b, 2b, 3b and 4b.

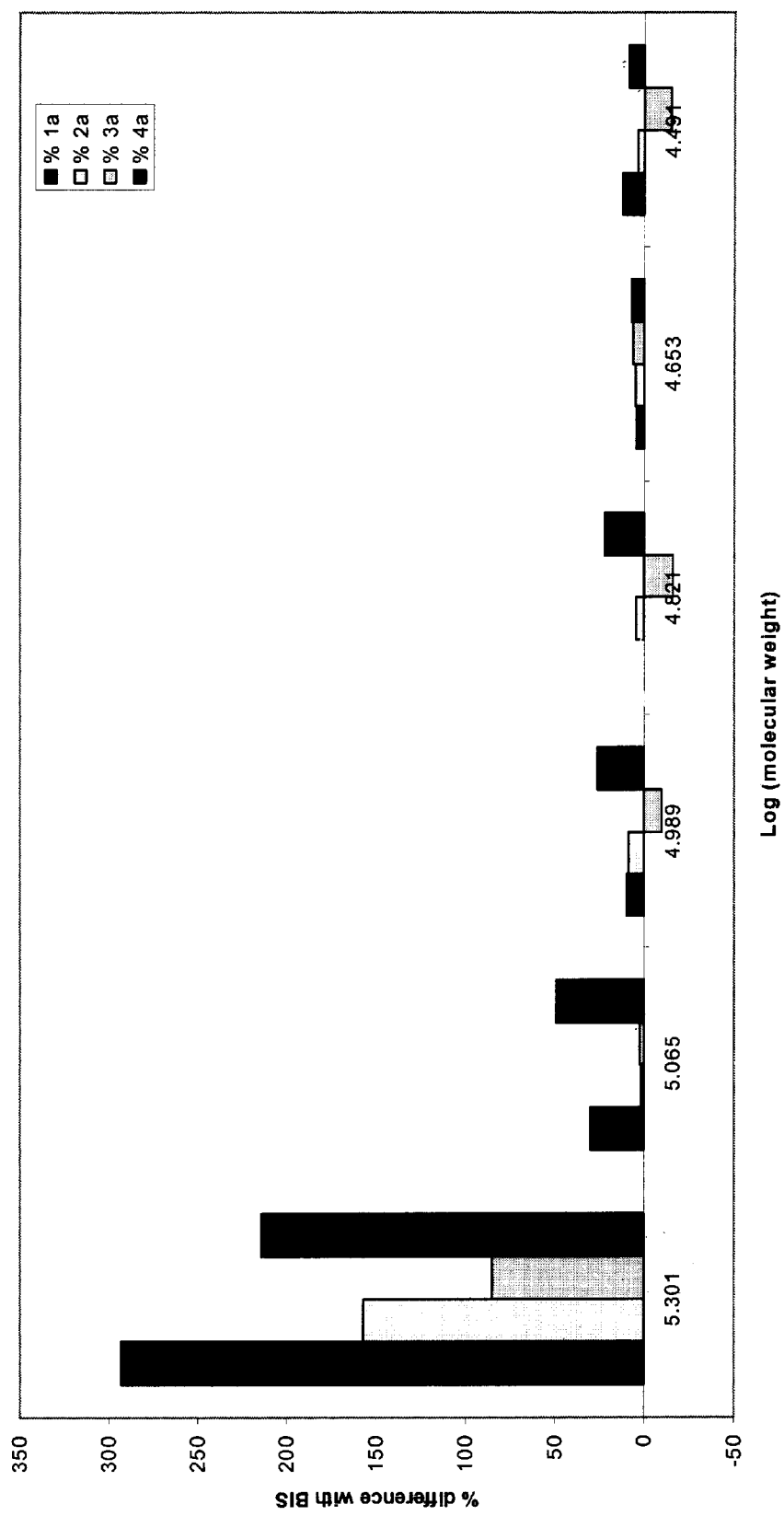
Figure 3: The % difference of gels crosslinked with 1a, 2a, 3a and 4a where all the double bonds have the same reactivity.

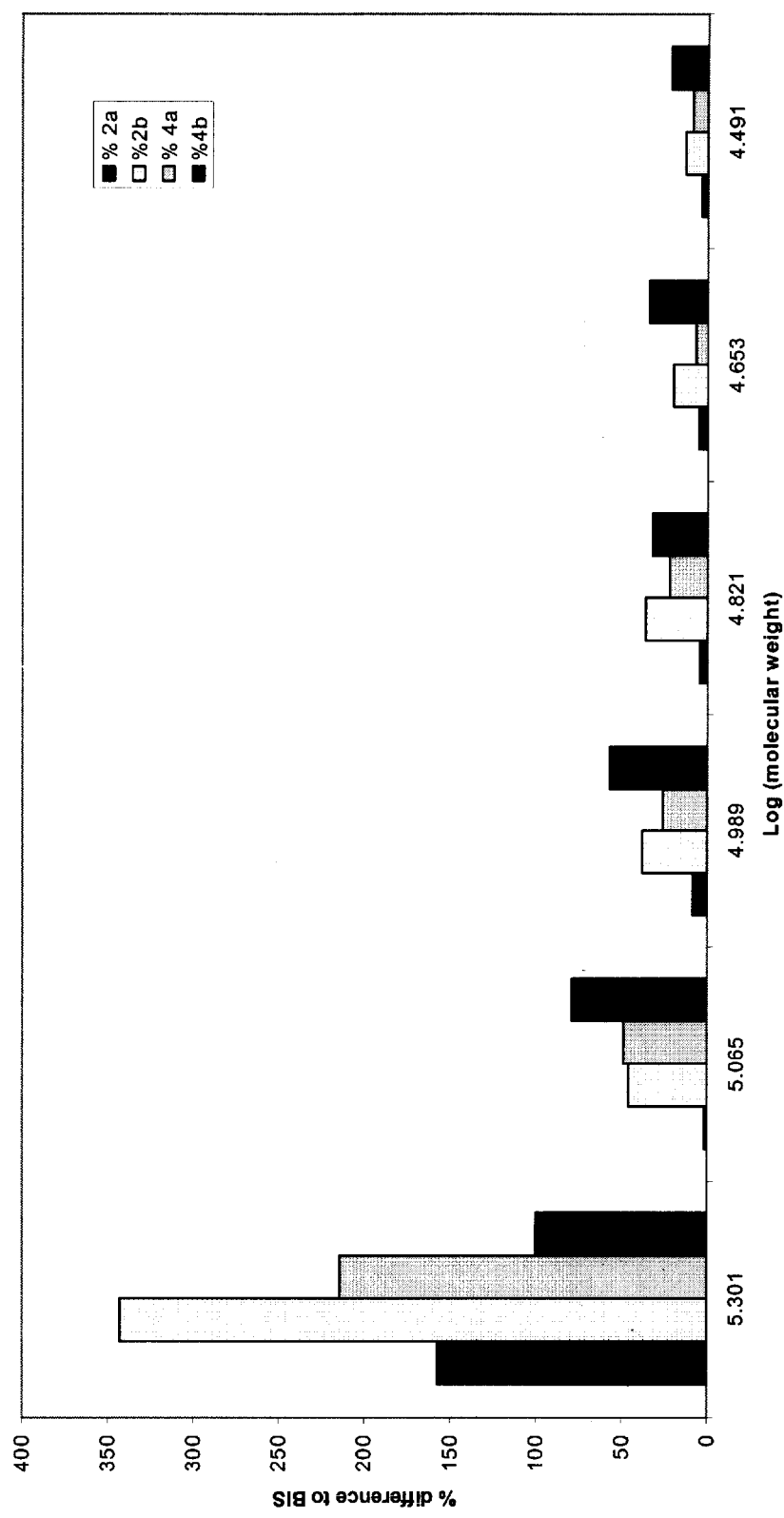
Figure 4: : The % difference of gels crosslinked with 2a, 2b, 4a and 4b where the double bonds have different reactivity.

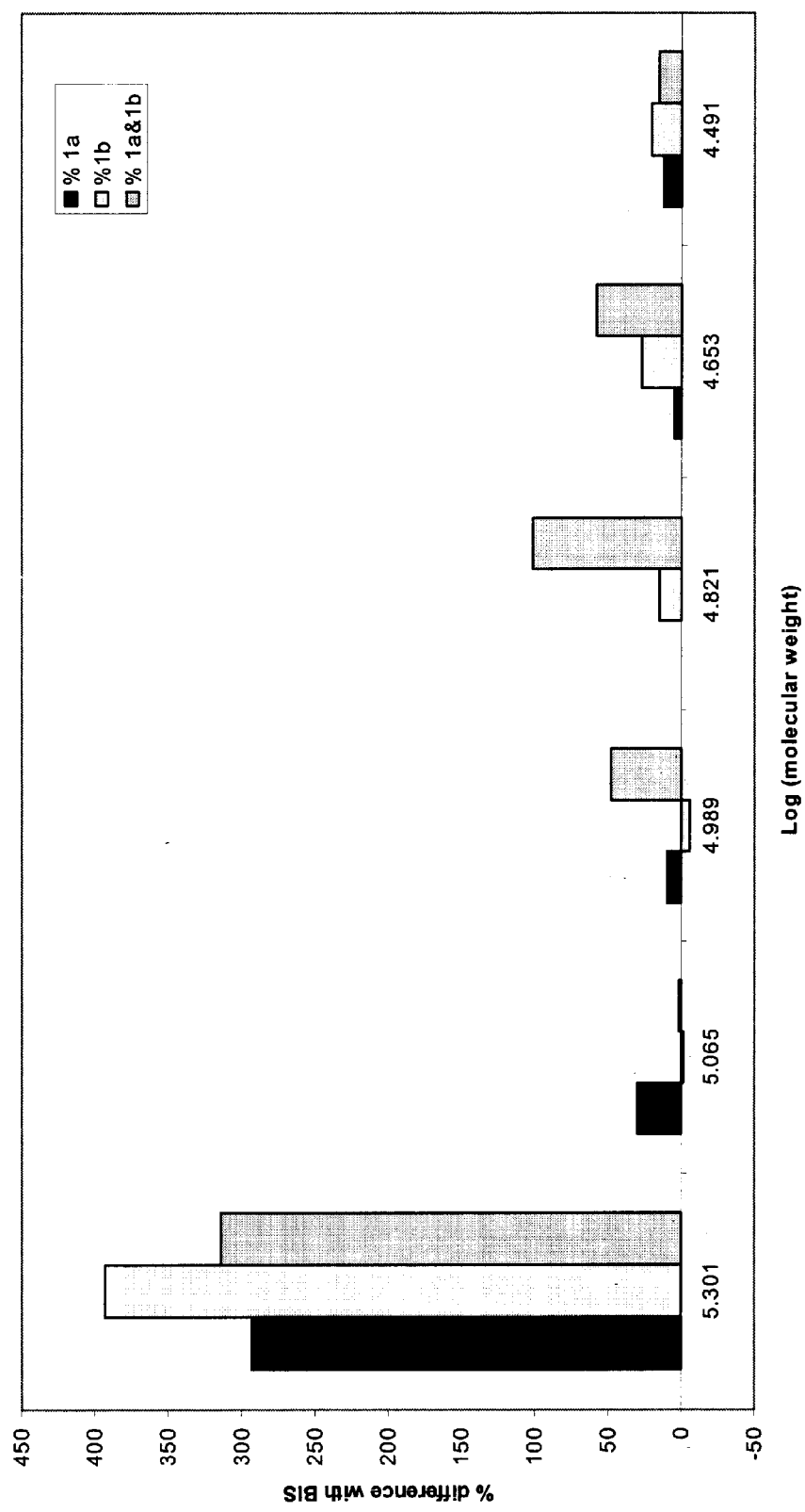
Figure 5: : The % difference of gels crosslinked with 1a, 1b and their mixture 1a with 1b in a 1:1 mixture.

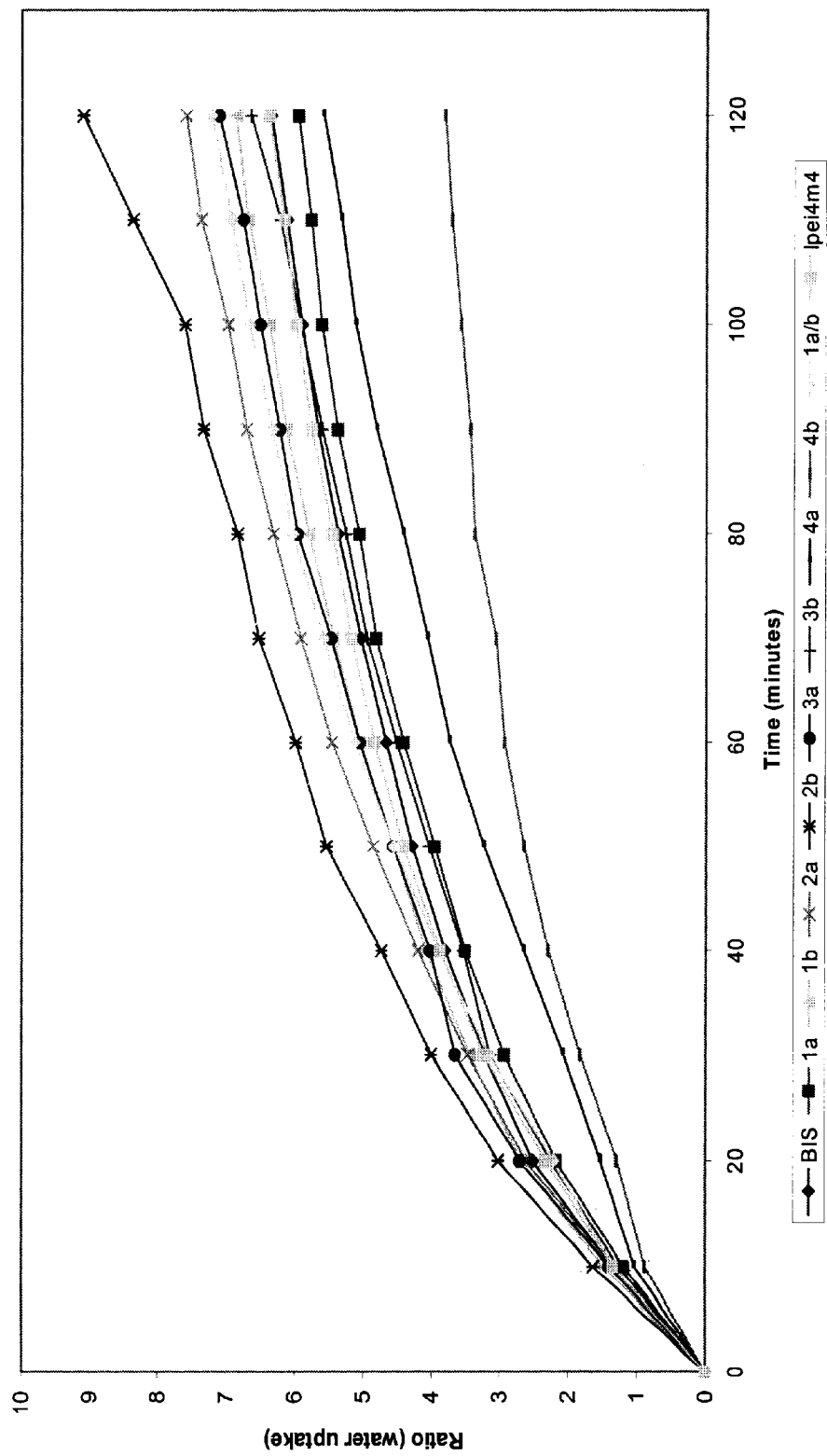
Figure 6: The ratio of water uptake plotted against time for polyacrylamide gels crosslinked with the crosslinkers above.

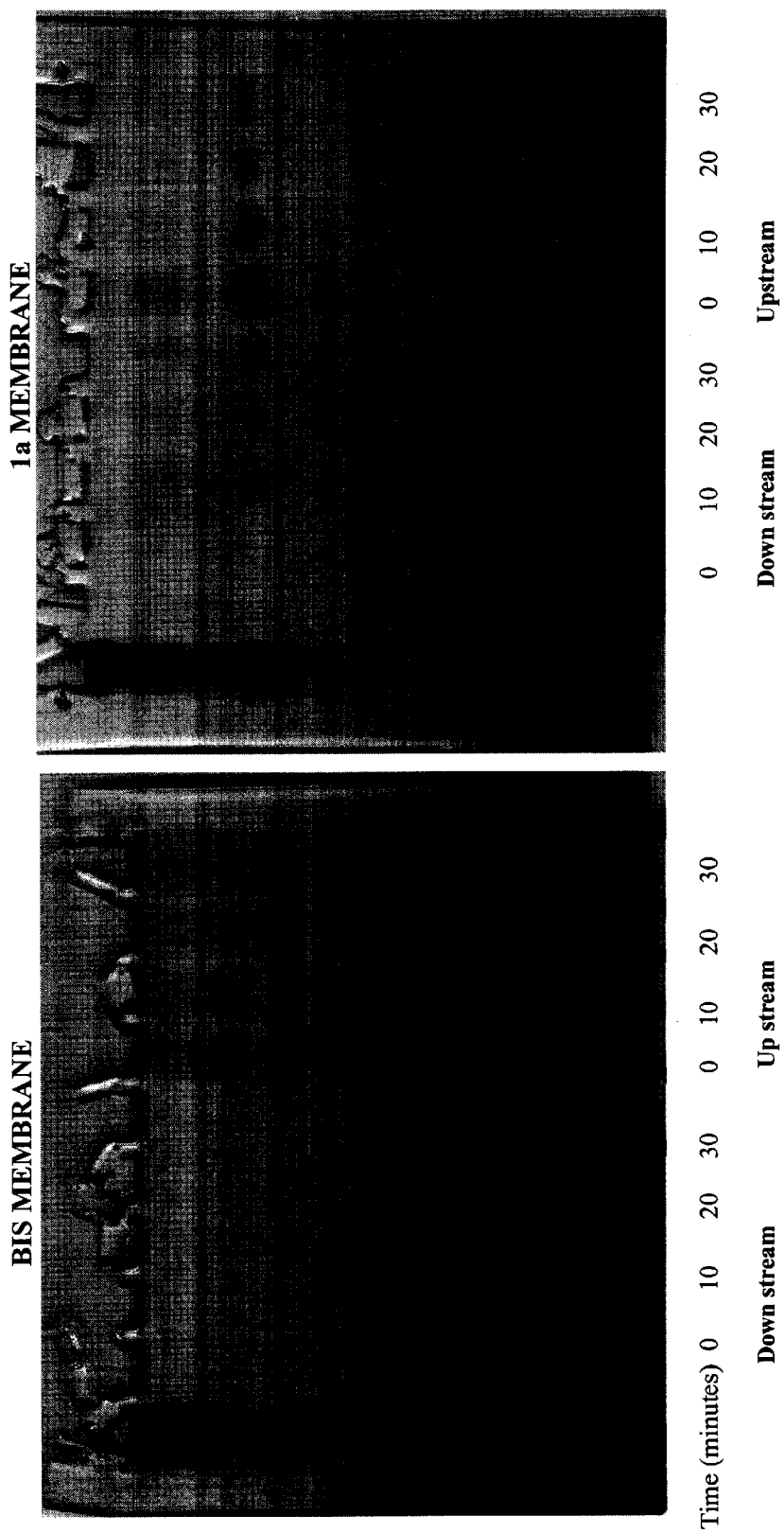
Figure 7: The separation and migration pattern of the protein molecular weight marker samples taken from the Gradiflow unit after electrophoresis by SDS-PAGE.

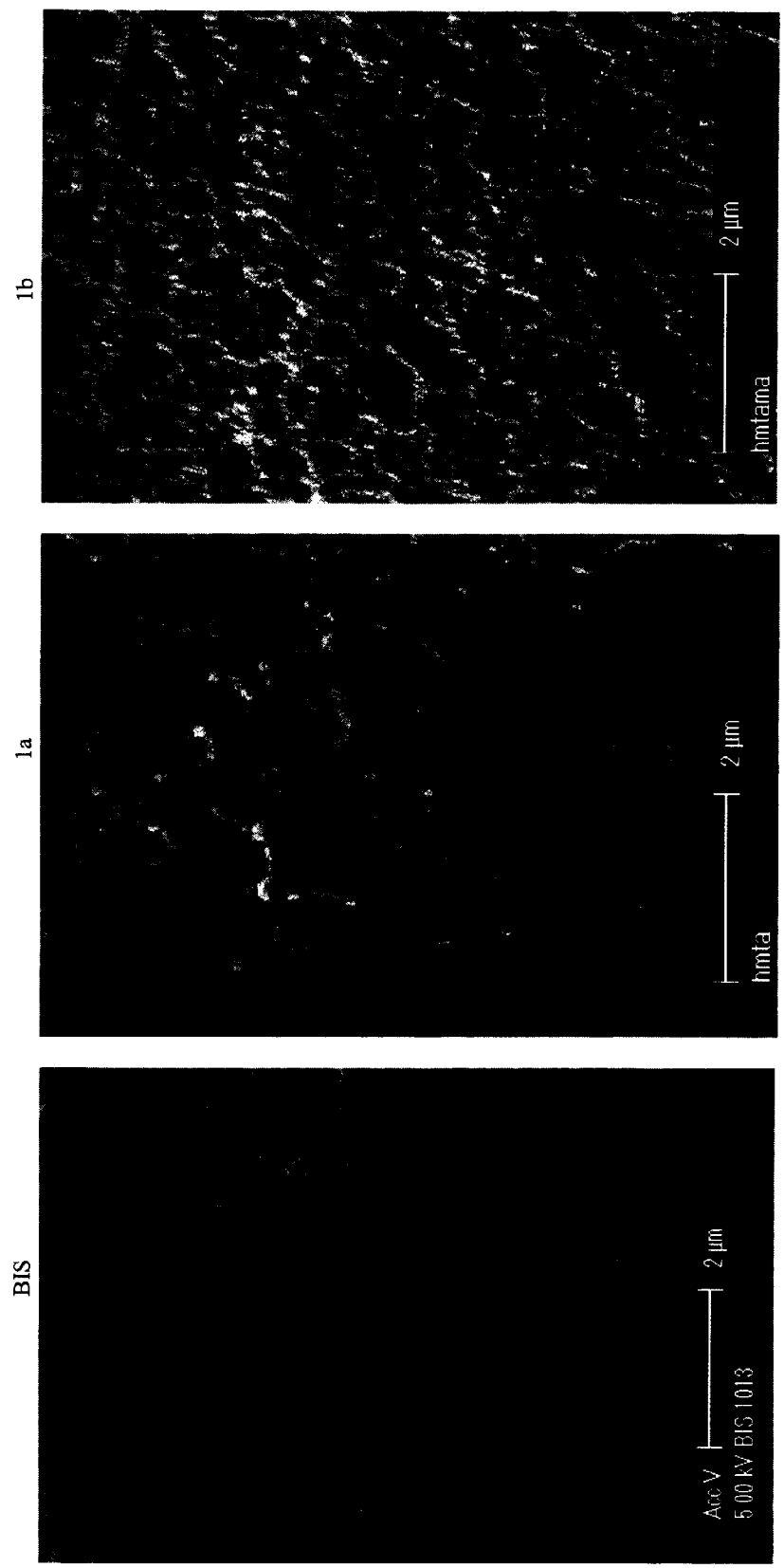
Figure 8: The SEM images obtained for polyacrylamide gels crosslinked with BIS, 1a and 1b.

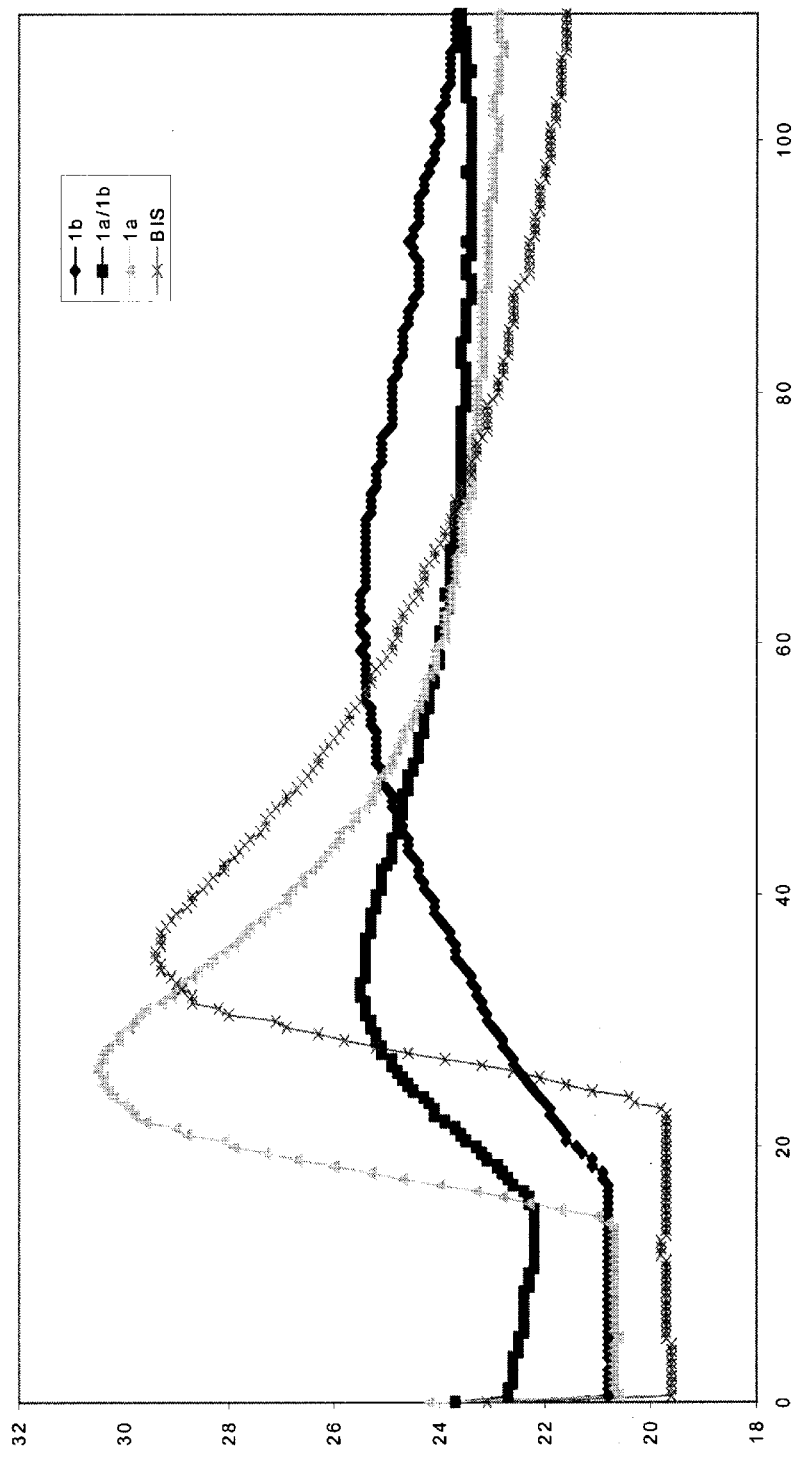
Figure 9: The temperature profile obtained during a free radical polymerization between acrylamide and the crosslinker BIS, 1a, 1b and the mixture 1a with 1b (1:1).

POLYMER GELS AND METHODS FOR THEIR PREPARATION

TECHNICAL FIELD

This invention relates to polymer gels and membranes. In particular it relates to polymer gels and membranes that are suitable for separation of molecules. The invention is also concerned with the preparation of novel polymer gels and membranes, the separation of molecules by techniques such as electrophoresis using these gels and membranes, and crosslinking agents useful in their preparation. The invention also relates to polymer gels of interest in areas that include bio-compatible applications such as prosthetic devices and optical and eye lenses.

The invention is especially suitable for electrophoretic applications and accordingly, for convenience, the invention will be further described with reference to electrophoresis. It is to be understood, however, that the gels, membranes, processes and crosslinking agents of the present invention are not so limited.

BACKGROUND OF THE INVENTION

Polyacrylamide gels used for electrophoresis are conventionally prepared by the copolymerization of the acrylamide (AAm) with methylene-bis-acrylamide (BIS) as the crosslinker (Scheme 1).

Scheme 1

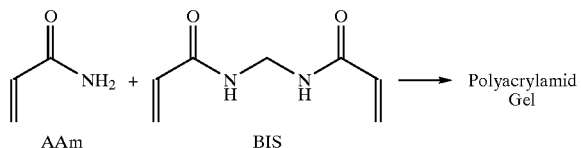

Such polyacrylamide gels have a number of limitations in electrophoretic applications, such as a limited porosity range[1], high background silver staining[2], low resistance to hydrolysis when stored in alkaline media, and restriction to concentration of the gel solution due to the lack of clarity.

Since both double bonds of BIS are of the same type, their reactivities are essentially the same. We have previously found an improvement in the separation of polyacrylamide gels when they are prepared using particular asymmetrical crosslinking agents (see PCT/AU97/00437, the disclosure of which is incorporated herein by reference).

DISCLOSURE OF THE INVENTION

We have now discovered that using multifunctional crosslinkers, that is crosslinkers having at least three crosslinkable functional groups, gives some unexpected improved properties. These improvements include:

1) Greater control when designing gels with a different pore size range;
2) Control of pore size distribution;
3) Greater resistance to hydrolysis in alkaline media;
4) Greater clarity of gels prepared with high concentration of the crosslinkers;
5) Reduced background after silver staining.

Accordingly, in one aspect, the present invention provides a crosslinked polymer gel formed from a least one monomer and at least one crosslinker having at least three crosslinkable functional groups, wherein at least one of the crosslinkable functional groups is an acryloyl or methacryloyl group as hereinafter defined.

The said at least three crosslinkable functional groups of the crosslinker may be the same or different.

The crosslinker may be a linear, branched or cyclic compound. Preferably all functional groups of the crosslinker have an ethylenic double bond. More preferably, the crosslinker has at least three acryloyl functional or methacryloyl groups or a combination thereof. Preferably, each acryloyl or methacryloyl group is attached to a nitrogen or oxygen atom.

The crosslinked polymer gel may be formed in the presence of one or more conventional crosslinker(s).

The monomer or monomers used to prepare the gel may be any suitable monomer. The gel may be formed from two or more different monomers.

The crosslinked polymer gel may be prepared from one or more monomers having the formula $H_2C=CR_5$—CO—$NR_3R_4$ where $R_3$, $R_4$ are each independently H, alkyl, alcohol (—$(CH_2)_a$—OH), or ester (—$(CH_2)_a$—$OCH_3$), where n is 1–6, and $R_5$ is H or optionally substituted alkyl. Examples of monomers include acrylamide, acrylamide derivatives or acrylamide substitutes known to the art such as N,N-dimethylacrylamide, methacrylamide, N-methyloylacrylamide, propylacrylamide, dipropyl acrylamide, isopropyl acrylamide, diisopropyl acrylamide, lactyl acrylamide, methoxyacrylamide and mixtures thereof. Preferably the, or at least one of, the monomer(s) is acrylamide.

In a preferred form of the invention, the crosslinker used in the crosslinked polymer gel of the invention is a compound selected from Formula I and/or Formula II

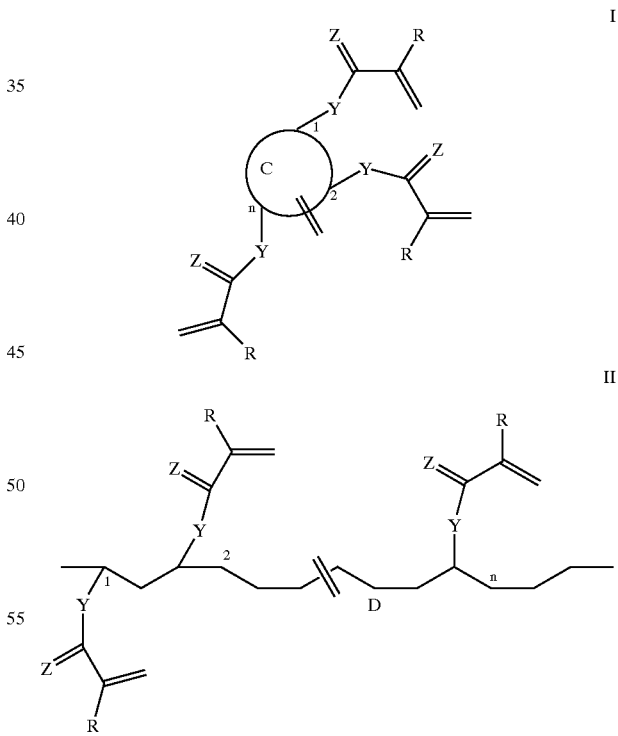

wherein, in Formula I:

C represents a ring structure of the crosslinker molecule which is connected with at least 3 functional groups —Y—CZC(R)=$CH_2$ which functional groups may be the same or different;

Y in each functional group may be the same or different and selected from a single bond, N, O or S;

Z in each functional group may be the same or different and selected from O or S; or Z may be two hydrogens, a hydrogen and an optionally substituted alkyl, or two optionally substituted alkyl groups; and R in each functional group may be the same or different and selected from hydrogen or substituted or unsubstituted alkyl, preferably H or $CH_3$.

Ring C may be a 3 to 12-membered carboxyclic or heterocyclic ring. Preferably C is a six-membered heterocyclic ring. The heteroatom)s) in the heterocyclic ring may be independently selected from N, O or S. Examples of suitable ring structures include heterocyclic amines and oxides. Y in each functional group may be the same or different and selected from N, O or S when it is connected to a carbon atom that is part of the ring system. Y may be a single bond if the functional group is connected to a ring nitrogen.

Preferably, each functional group is connected to the ring C through a heteroatom. Preferably the heteroatom is N. The heteroatom may be a ring atom or a heteroatom of a ring C substituent.

Ring C may be a heterocyclic nitrogen-containing ring, for example, a ring having the structure:

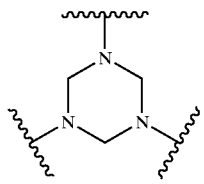

In Formula II:

D represents a backbone chain of the crosslinker which is connected with at lest three functional groups —Y—CzC(R)=$CH_2$ which functional groups may be the same or different;

Y in each functional group may be the same or different and selected from a single bond, N, O or S;

Z in each functional group may be the same or different and selected from O or S; and R in each functional group may be the same or different and selected from hydrogen or substituted or unsubstituted alkyl, preferably H or $CH_3$.

The backbone chain of the compound of Formula II may be linear, branched or cyclic. The backbone may optionally be substituted and/or optionally interrupted by one or more heteroatoms O, S, N and/or one or more aromatic, saturated or unsaturated carboxyclic or heterocyclic radicals. The backbone may be a small molecule (monomer), oligomer or polymer. Y in each functional group may be the same or different and selected from N, O or S if the backbone chain contains only carbons. Y may also be a single bond if the backbone chain contains N within the chain or contains N or O or S at the ends of the main backbone chain or a branched chain to connect with the functional groups.

Preferably, each functional group is connected to the backbone via a heteroatom. Preferably, the heteroatom is N. The heteroatom may be a heteroatom interrupting the backbone, a heteroatom at the end(s) of the backbone chain, or it may be a heteroatom of a branching group of the backbone chain.

The backbone chain may be a relatively small molecule of sufficient length to allow substitution of 3 to about 6 crosslinkable functional groups.

The backbone chain may be a linear, branched or cyclic oligomer having approximately 3–20 repeat units, which may be the same or different. Examples of suitable oligomer backbones are polyalkylene imine oligomers (eg polyethylene imine oligomers) and polyalkylene oxides oligomers.

The backbone chain of the compound of formula II may be a linear, branched or cyclic polymer having a length up to about one million atoms. The polymer may be a polyalkylene imine (eg polyethylene imine) or polyalkylene oxide. The polymer may have a degree of substitution of up to 100% of the functional group.

The term "acryloyl" as used herein denotes the group $CH_2$=CH—CO— and;

The term "methacryloyl" as used herein denotes the group $CH_2$=C(R)—CO—, where R is optionally substituted alkyl, preferably C1–C4 alkyl, more preferably $CH_3$.

In this specification the term "optionally substituted" means that a group may or may not be further substituted with one or more groups selected from alkyl, cycloalkyl, alkenyl, alkynyl, halo, haloalkyl, haloalkynyl, hydroxy, alkoxy, alkenyloxy, haloalkoxy, haloalkenyloxy, nitro, amino, nitroalkyl, nitroalkenyl, nitroalkynyl, nitroheterocyclyl, alkylamino, dialkylamino, alkenylamine, alkynylamino, acyl, alkenacyl, alkynylacyl, acylamino, diacylamino, acyloxy, alkylsulphonyloxy, heterocyclyl, heterocycloxy, heterocyclamino, haloheterocyclyl, alkylsulphenyl, carboalkoxy, alkylthio, acylthio, phosphorous-containing groups such as phosphono and phosphinyl.

The term "alkyl", used either alone or in compound words such as "haloalkyl" or "alkylthio", denotes straight chain or branched $C_{1-6}$ alkyl groups. Examples include methyl, ethyl, propyl, isopropyl and the like.

The term "alkoxy" denotes straight chain or branched alkoxy, preferably $C_{1-10}$ alkoxy. Examples include methoxy, ethoxy, n-propoxy, isopropoxy and the different butoxy isomers.

The term "alkenyl" denotes groups formed from straight chain, branched or mono—or polycyclic alkenes including ethylenically mono—or poly—unsaturated alkyl or cycloalkyl groups as previously defined, preferably $C_{2-10}$ alkenyl. Examples of alkenyl include vinyl, allyl, 1-methylvinyl, butenyl, iso-butenyl, 3-methyl-2-butenyl, 1-pentenyl, cyclopentenyl, 1-methyl-cyclopentenyl, 1-hexenyl, 3-hexenyl, cyclohexenyl, 1-heptenyl, 3-heptenyl, 1-octenyl, cyclooctenyl, 1-nonenyl, 2-nonenyl, 3-nonenyl, 1-decenyl, 3-decenyl, 1,3-butadienyl, 1-4,pentadienyl, 1,3-cyclopentadienyl, 1,3-hexadienyl, 1,4-hexadienyl, 1,3-cyclohexadienyl, 1,4-cyclohexadienyl, 1,3-cycloheptadienyl, 1,3,5-cycloheptatrienyl, or 1,3,5,7-cyclooctatetraenyl.

The term "halogen" denotes fluorine, chlorine, bromine or iodine, preferably chlorine or fluorine.

The term "acyl" used either alone or in compound words such as "acyloxy", "acylthio", "acylamino" or "diacylamino" denotes carbamoyl, aliphatic acyl group and acyl group containing a heterocyclic ring which is referred to as heterocyclic acyl, preferably $C_{1-10}$ acyl. Examples of acyl include carbamoyl; straight chain or branched alkanoyl, such as formyl, acetyl, propanoyl, butanoyl, 2-methylpropanoyl, pentanoyl, 2,2-dimethylpropanoyl, hexanoyl, heptanoyl, octanoyl, nonanoyl, decanoyl; alkoxycarbonyl, such as methoxycarbonyl, ethoxycarbonyl, t-butoxycarbonyl, t-pentyloxycarbonyl or heptyloxycarbonyl; cycloalkylcarbonyl such as cyclopropylcarbonyl cyclobutylcarbonyl, cyclopentylcarbonyl or cyclohexylcarbonyl; alkylsulfonyl, such as methylsulfonyl or ethylsulfonyl, alkoxysulfonyl, such as methoxysulfonyl or ethoxysulfonyl; heterocyclycarbonyl; heterocyclylalkanoyl, such as pyrrolidinylacetyl, pyrrolidinylpropanoyl, pyrrolidinylbutanoyl, pyrrolidinylpentanoyl, pyrrolidinylhexanoyl or thiazolidinylacetyl; heterocyclylalkenoyl, such as heterocyclylpropenoyl, heterocyclylbutenoyl, heterocyclylpentenoyl or heterocyclylhexenoyl; or heterocyclylglyoxyloyl, such as, thiazolidinylglyoxyloyl or pyrrolidinylglyoxyloyl.

An example of a compound of Formula I is compound 1.

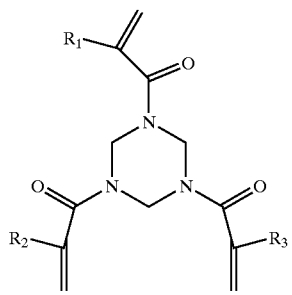

wherein $R_1$, $R_2$ and $R_3$, which may be the same or different, are selected from H or optionally substituted alkyl.

An example of a compound of Formula II is compound 2.

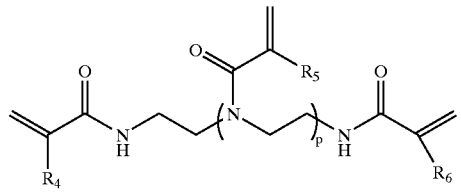

wherein $R_4$, $R_5$ and $R_6$, which may be the same or different, are selected from H or optionally substituted alkyl and p is 1 to about 6.

A further example of a compound of Formula II is

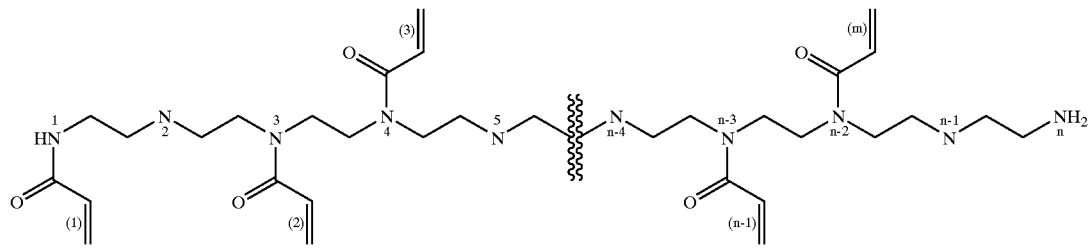

wherein n represents the number of repeating unit of the polyethylene imine backbone and m represents the number of acryloyl or methacryloyl groups substituted on the backbone, m and n being at least 3.

The polymer gel according to this invention may be an electrophoresis gel, which may or may not have a porosity gradient or composition gradient. The gradient may be achieved by using different concentrations of the polymer gel or by altering the ratio of crosslinker to monomer.

The electrophoresis gel may have a porosity gradient suitable for gradient gel electrophoresis. See for example, *Polyacrylaminde Gel Electrophoresis across a Molecular Sieve Gradient* Margolis, J., Kenrick, K. G., Nature, 214, 1967, p 1334–1336; *Polyacrylamide Gel Electrophoresis in a Continuous Molecular Sieve Gradient*, Margolis, J., Kenrick, K. G., Analytical biochemistry, 25, 1968, p347–362 and *Practical System for Polyacrylamide Gradient Gel electrophoresis*, Margolis, J., Laboratory Practice, 22, p107–109, 1973, the disclosures of which are incorporated herein by reference.

The polymer gel of the present invention may be in the from of a membrane.

Accordingly, in a further aspect the present invention provides an electrophoretic membrane including an electrophoretic gel in accordance with the present invention formed on a porous substrate.

The substrate may have a larger pore size than that of the electrophoretic medium. The substrate may be a porous paper or fabric. The substrate may be woven or non-woven sheet, for example, a non-woven PET.

The greater control on designing gels with a different pore size range and/or distribution provided by the polymer gels of the present invention make them particularly suitable for use in electrophoresis separation method and apparatus described in Gradipore Limites's U.S. Pat. No. 5,039,386 and U.S. Pat. No. 5,650,055, the disclosures of which are incorporated herein in their entirety. This technology is incorporated into Gradipore Limited's Grandiflow™ technology. The technology allows for the separation of macromolecules such as proteins, nucleotides and complex sugars. It can be used for size separation, concentration and dialysis. A commercially available form of this technology is Gran-dipore Limited's Babyflow™ BF200 unit. The hear of Gradiflow™ is a membrane cartridge, which consists of three polyacrylamide-based membranes. The top and bottom membranes are small pore size restriction membranes. These membranes allow the movement of small ions, The middle membrane is the separating membrane, which varies with the particular application. This middle membrane usually has a larger, but defined pore size. It is in this middle membrane that the membrane of the present invention may have particular application. For specific applications, the membrane may be charged or have an affinity ligand embedded within the membrane.

In yet a further aspect of the present invention, there is provided a method of preparing a crosslinked polymer gel, said method including the step of subjecting one or more monomers to crosslinking polymerization in the presence of one or more crosslinking agents of Formula I and/or Formula II set out above.

The method of the present may be carried out in the presence of one or more other crosslinkers conventionally used in the art.

Preferable polymerizations are carried out in a solution of the monomer or monomers with the crosslinking agent(s). For most applications involving polyacrylamide gels, the solvent will be water. However, other solvents including DMF, THF, alcohol and other water miscible systems may be required.

The polymer gels according to this invention may be useful for separating molecules, especially charged species, or species capable of bearing a charge such as biomolecules.

Accordingly, in a further aspect, the invention provides a method of separating molecules including:

providing a crosslinker polymer gel by combing one or more monomers with a crosslinker of Formula I and/or Formula II, optionally with one or more other crosslinker(s), subjecting the monomer solution to polymerization and crosslinking, in the presence of an initiator, placing a sample containing the molecules to be separated onto the gel, and subjecting the gel and sample to a separation technique.

The polymerization may be initiated by well known means such as UV, photopolymerization, redox or thermal initiation systems.

The present invention is not limited to obtaining a crosslinked polymer gel using a free radical polymerization method. The double bonds of the crosslinkers can be crosslinked with each other to form gels in other non radical polymerization reactions such as the 'Michael addition'. The Michael addition involves a conjugate addition between a nucleophile such as a diamine with an α,β-unsaturated carbonyl such as the double bond of an acryloyl or methancryloyl group. One or more crosslinking agents of Formula I and/or Formula II and/or in the presence of one or more other crosslinkers conventionally used in the art, with or without a nucleophile possessing two or more reactive nucleophilic groups. A nucleophile can be a diamine $NH_2$—$(R)_a$—$NH_2$ where R in each diamine is a $CH_2$ group and n is between 1–10 and can produce a 3-gel network as shown in scheme 2. Furthermore, the crosslinking agent of Formula I and/or Formula II can undergo self crosslinking reactions under the Michael addition conditions, where the $NH_2$ group on the crosslinker acts as the nucleophile (scheme 3).

Scheme 2

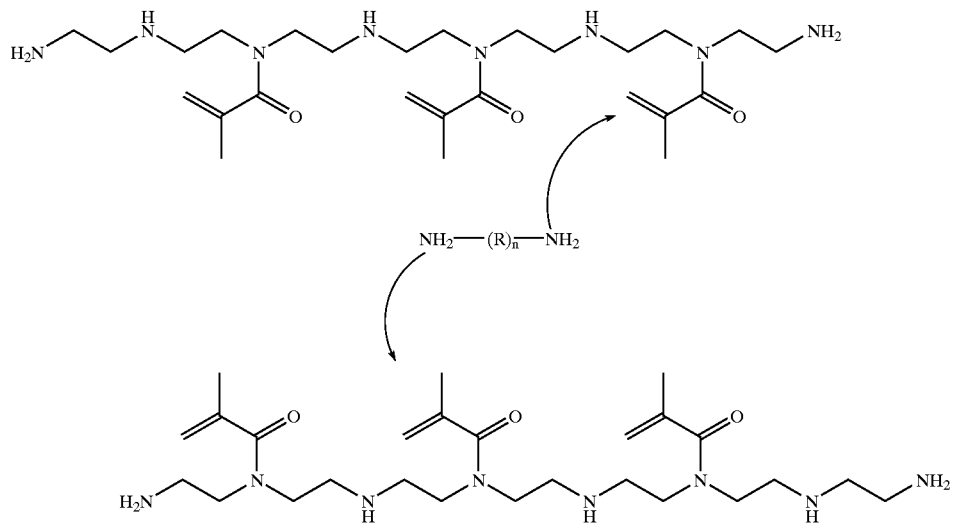

Scheme 3

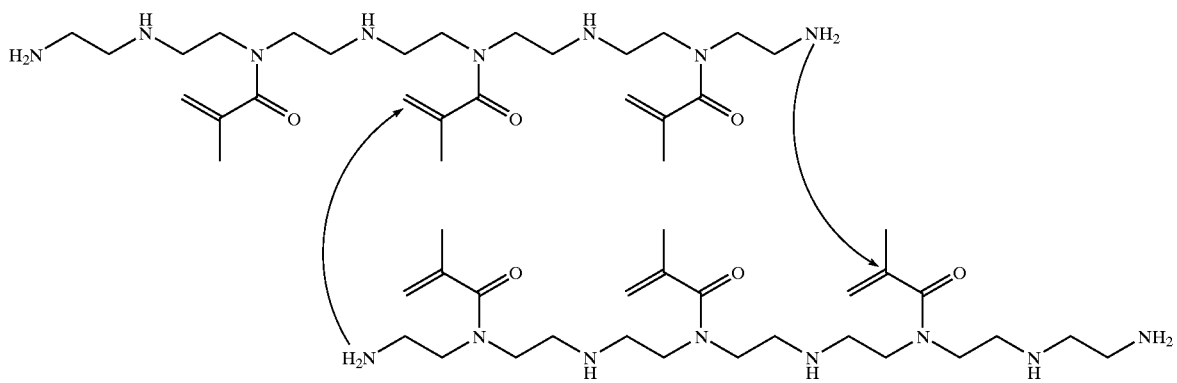

Preferably the separation technique is electrophoresis.

The electrophoresis technique employed may be any of those known to the art, including one—, two—and multi-dimensional techniques. The electrophoresis technique may be gradient gel electrophoresis.

The separation technique may be that described in Gradipore Limited's U.S. Pat. No. 5,039,386 and U.S. Pat. No. 5,650,055.

The molecule separated using the separation method of the invention may be a bio-molecule. The term "biomolecule" as herein denotes biological molecules such as proteins, enzymes and other peptides, genetic material such as chromosomal material, genomic DNA, cDNA, mRNA, tRNA and other oligo—and polynucleotides. The term includes naturally occurring biological molecules in addition to fragments and recombinant derivatives thereof.

The polymerization reaction between the monomers according to this invention is generally a free radical reaction, carried out in an aqueous medium, which can be initiated by any known initiator system, including initiator and co-initiator. Suitable free radical providing initiator systems include peroxides, such as benzoyl peroxide with or without a co-initiator; various persulfates, such as ammonium persulfate (APS); or azo-compounds such as azodiisobutyronitrile. Typical co-initiators when APS is used are amine such as $N,N,N^1,N^1$-tetramethylethylenediamine (TEMED) or dimethylaminopropionitrile (DMAPN). The polymerization may also be initiated by photopolymerization, UV or thermal initiation systems.

The gels according to this invention may include conventional additives known to the art as required by the techniques employed. These additives include, but are not limited to, detergents, for example, sodium dodecyl sulphate (SDS); denaturing agents, for example, urea; high molecular weight polymers, such as linear polyacrylamide; an low molecular weight species, such as glycerols, polyethylene glycol, polysaccharides, agarose and cellulose triacetates. The gel may also include a suitable buffer system.

In still a further aspect, the present invention provides a method for preparing a polymer gel having one or more preselected properties, the method including combining one or more monomers with a crosslinker of Formula I and/or Formula II, optionally with one or more other crosslinker(s), optionally in the presence of an initiator, and subjecting the monomer(s) and crosslinker(s) to polymerization and crosslinking, wherein the nature and/or amount of the crosslinker of Formula I and/or Formula II is selected to produce a gel having said one or more preselected property(ies).

The preselected property of properties may be selected from one or more of:
1) pore size range;
2) pore size distribution;
3) resistance to hydrolysis in alkaline media;
4) clarity, of gels (eg by using high concentration of the crosslinker(s); and
5) Reduced background after silver staining.

The preselected property e.g. porosity, may be achieved by varying the number and/or type of functional groups present on the crosslinker and/or the structure of the crosslinker (eg, linear, cyclic or branched). The preselected property may be achieved by using a combination of two or more different crosslinking agents in accordance with the present invention, the crosslinking agents differing in their backbone and/or ring and/or their functional groups. Some specific examples of these various combinations are given below:

A crosslinked polymer gel formed from at least one crosslinker and optionally at least one monomer, wherein the at least one crosslinker has at least three functional groups $CH_2=C(R)-CO-$, where R is H or $CH_3$, wherein at least one functional group is attached to a nitrogen and at least one other functional group is attached to a heteroatom other than nitrogen.

A crosslinked polymer gel formed from a mixture of crosslinkers and optionally at least one monomer, wherein the mixture of crosslinkers comprises (a) at least one crosslinker having at least three functional groups $CH_2=CH-CO-$ each attached to a nitrogen and (b) at least one crosslinker having at least three functional groups $CH_2=C(CH_3)-C-$ each attached to a nitrogen.

A crosslinked polymer gel formed from a mixture of crosslinkers and optionally at least one monomer, wherein the mixture of crosslinkers comprises (a) at least one crosslinker having at least three functional groups $CH_2=CH-CO-$, wherein at least one functional group $CH_2=CH-CO-$ is attached to a nitrogen and at least one other functional group $CH_2=CH-CO-$ is attached to a heteroatom other than nitrogen and (b) at least one crosslinker having at least three functional groups $CH_2=C(CH_3)-CO-$, wherein at least one of functional groups $CH_2=C(CH_3)-CO-$ is attached to a nitrogen and at least one other functional group $CH_2=C(CH_3)-CO-$ is attached to a heteroatom other than nitrogen.

A crosslinked polymer gel formed from a mixture of crosslinkers and optionally at least one monomer, wherein the mixture of crosslinkers comprises (a) at least one crosslinker having at least three functional groups $CH_2=CH-CO-$, wherein each functional group $CH_2=CH-CO-$ is attached to a nitrogen and (b) at least one crosslinker having at least three functional groups $CH_2=C(CH_3)-CO-$ wherein at least one of functional groups $CH_2=C(CH_3)-CO-$ is attached to a nitrogen and at least one other functional group $CH_2=C(CH_3)-CO-$ is attached to a heteroatom other than nitrogen.

A crosslinked polymer gel formed from a mixture of crosslinkers and optionally at least one monomer, wherein the mixture of crosslinkers comprises (a) at least one crosslinker having at least three functional groups $CH_2=CH-CO-$, wherein at least one functional group $CH_2=CH-CO-$ is attached to a nitrogen and at least one other functional group $CH_2=CH-CO-$ is attached to a heteroatom other than nitrogen and (b) at least one crosslinker having at least three functional groups $CH_2=C(CH_3)-CO-$, wherein each functional groups $CH_2=C(CH_3)-CO-$ is attached to a nitrogen.

The polymer gel of the present invention may have a larger pore size compared to that of polymer gels prepared using the conventional AAm/BIS system. Moreover the polymer gel of the invention may have a high surface area of the polymer network and a capability of absorbing more solvents.

In yet a further aspect the present invention provides novel compounds suitable for use as crosslinkers, the compounds being accordance with Formula I or Formual II:

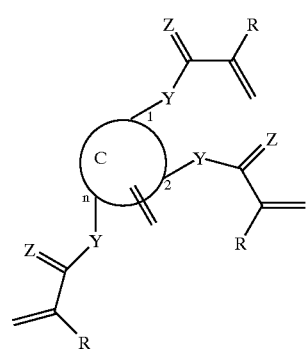

I

II

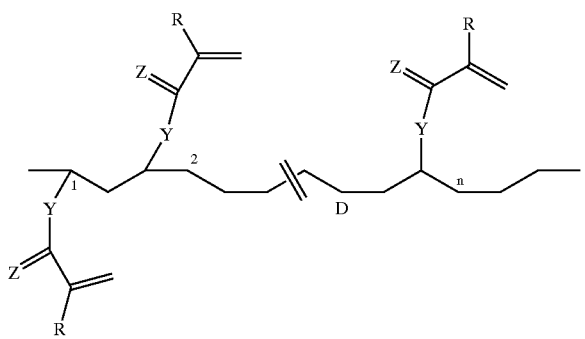

wherein, in Formula I:

C represents a ring structure of the crosslinker molecule which is connected with at least 3 functional groups —Y—CZC(R)=CH$_2$ which functional groups may be the same or different;

Y in each functional group may be the same or different and selected from single bond, N, O or S;

Z in each functional group may be the same or different and selected from O or S; or Z may be two hydrogens, a hydrogen an optionally substituted alkyl, or tow optionally substituted alkyl groups; and R in each functional group may be the same or different and selected from hydrogen or optionally substituted alkyl, preferably H or CH$_3$, but excluding the compounds hexamethylenetriamine triacrylate and hexamethylenetriamine trimethacrylate.

Ring C may be a 3 to 12-membered carboxyclic or heterocyclic ring. Preferably C is a six-membered heterocyclic ring. The heteroatom(s) in the heterocyclic ring may be independently selected from N, O or S. Examples of suitable ring structures include heterocyclic amines and oxides. Y in each functional group may be the same or different and selected from N, O or S when it is connected to a carbon atom that is part of the ring system. Y may be a single bond if the functional group is connected to ring nitrogen.

Ring C may be heterocyclic nitrogen containing ring, for example, a ring having the structure:

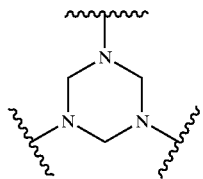

In Formula II:

D represents a backbone chain of the crosslinker which is connected with at lest three functional groups —Y—CZC(R)=CH$_2$ which functional groups may be the same or different;

Y in each functional group may be the same or different and selected from a single bond, N, O or S;

Z in each functional group may be the same or different and selected from O or S; and R in each functional group may be the same or different and selected from hydrogen or optionally substituted alkyl, preferably H or CH$_3$.

The backbone chain of the compound of Formula II may be linear, branched or cyclic. The backbone may optionally be substituted and/or optionally interrupted by one or more heteroatoms O,S,N and/or one or more aromatic, saturated or unsaturated carbocylic or heterocyclic radicals. The backbone may be a small molecule (monomer), oligomer or polymer. Y in each functional group may be the same or different and selected from N, O or S if the backbone chain contains only carbons. Y may also be a single bond if the backbone chain contains N or O or S at the ends of the main backbone chain or a branched chain to connect with the functional groups.

Preferably, each functional group is connected to the backbone via a heteroatom. Preferably, the heteroatom is N. The heteroatom may be a heteroatom interrupting the backbone or it may be a heteroatom of a branching group of the backbone chain.

The backbone chain may be a small molecule of sufficient length to allow substitution of 3 to about 6 crosslinkable functional groups.

The backbone chain may be a linear, branched or cyclic oligomer having approximately 3–20 repeat units, which may be the same or different. Examples of suitable oligomer backbones are polyalkyleneimine oligomers (eg polyethyleneimine oligomers) and polyalkylene oxides oligomers.

The backbone chain of the compound of formula II may be a linear, branched or cyclic polymer having a length up to about a million atoms. The polymer may be a polyalkyleneimine (eg polyethyleneimine) or polyalkylene oxide. The polymer may have a degree of substitution of up to about 80% of the functional groups.

Particularly preferred compounds of Formula II of the invention are trimethacyloyldiethylenetriamine, triacryloyltris(2-aminoethyl)amine, trimethacryloyl-tris(2-aminoethyl)amine and multi-acryloyl-substituted polyethyleneimines of the formula

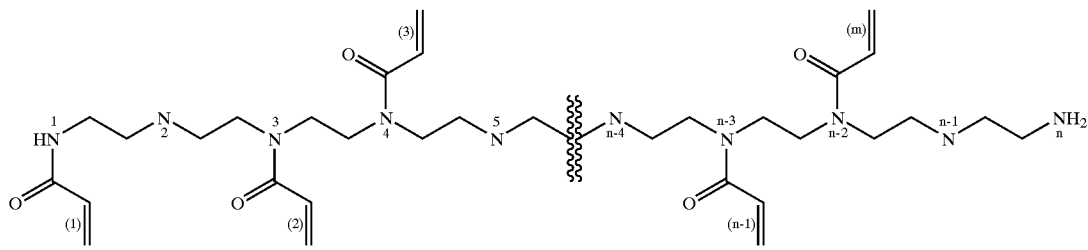

wherein n represents the number of repeating unit of the polyethylene imine backbone and m represents the number of acryloyl or methacryloyl groups substituted on the backbone, m and n being at least 3.

The crosslinking agents according to this invention may be prepared by conventional methods. The number and amount of the functional groups, which may be similar or different, may be introduced on the same crosslinker, depending on the size of the molecules to be separated. The synthesis methodologies described below are particularly preferred and the present invention extends to these methods of synthesis.

The relative amount of the crosslinker to the monomer may be about 2–15%C but may vary from this amount depending on the desired properties of the gel formed.

The crosslinkers of the present invention have application in crosslinking of polymers other than polymer gels and accordingly in yet a further aspect, the present invention provides a crosslinked polymer formed from at least one monomer and at least one crosslinker having at least three crosslinkable functional groups, wherein at least one of the crosslinkable functional groups is an acryloyl group.

The following examples are provided for the purpose of further illustration of the present invention but are in no way to be taken as limiting the scope of the present invention.

BRIEF DESCRIPTION OF DRAWINGS

In the accompanying drawings:

FIG. 1 shows the structural formulae for crosslinkers in accordance with the present invention;

FIG. 2a is a graph of the Rf values plotted against the log of the molecular weight of the proteins separated on polyacrylamine gels crosslinked with BIS, 1a, 2a, 3a, 4a;

FIG. 2b is a graph of the Rf values plotted against the log of the molecular weight of the proteins separated on polyacrylamide gels crosslinked with BIS, 1b, 2b, 3b and 4b;

FIG. 3 is a bar graph showing the percentage (%) difference between a gel crosslinked with BIS and gels crosslinked with crosslinkers 1a, 2a, 3a and 4a in accordance with the present invention, where all double bonds have the same reactivity;

FIG. 4 is a bar graph showing the percentage (%) difference between a gel crosslinked with BIS and gels crosslinked with crosslinkers 2a, 2b, 4a and 4b in accordance the present invention where the double bonds have different reactivity;

FIG. 5 is a bar graph showing the percentage (%) difference between gels crosslinked with crosslinkers 1a, 1b and a 1:1 mixture of 1a and 1b;

FIG. 6 is a graph showing the ratio of water uptake plotted against time for polyacrylamide gels crosslinked with BIS and gels crosslinked with crosslinkers in accordance with the present invention;

FIG. 7 shows the separation and migration pattern of the protein molecular weight marker samples taken from a Gradiflow™ electrophoresis unit after electrophoresis by SDS-PAGE; using membranes made with BIS and 1a.

FIG. 8 shows SEM images obtained for polyacrylamide gels crosslinked with crosslinkers BIS, 1a and 1b; and FIG. 9 is a graph showing the temperature profile obtained during a free radical polymerization between acrylamide and the crosslinkers BIS, 1a, 1b and a 1:1 mixture of 1a and 1b.

DESCRIPTION OF EMBODIMENTS OF THE INVENTION

Synthesis of Crosslinkers

EXAMPLE 1

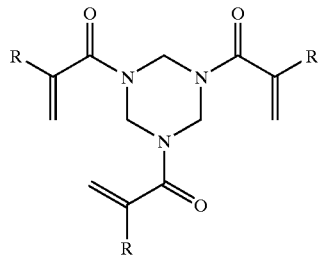

1a, R = H
1b, R = CH₃

1a. Hexamethyltriamine triacrylate[3]:

Acrylonitrile (6.60 g) and sulfuric acid (0.65 g) in carbon tetrachloride (25 ml) were brought to reflux at 70° C. To this, a solution of acrylonitrile (6.65 g) and s-trioxane (7.50 g) in carbon tetrachloride (25 ml) was added drop wise over 15 minutes. A white solid separated out before the addition was complete and the solution was then stirred for a further 1 hour under reflux. The reaction mixture was then cooled to room temperature and the white solid was collected by filtration and recrystallized from methanol to obtain (10.33 g, 49.69%) white crystal. $^1$H n.m.r. (CDCL$_3$):δ5.41 (6H, s) N—CH$_2$—N; 5.83 (3H, dd, j8.9, 1.6 Hz) CH$_a$H$_b$=CH; 6.37 (3H, dd, J 15.1, 1.6 Hz) CH$_{H=CH}$; 6.78 (3 H, dd, J 5.8, 10.6 Hz). CH$_{H=CH}$. $^{13}$C n, m, r, (CDCL$_3$): δ55.5 (N—CH$_2$—N); 126.1 (CH$_2$=CH); 130.9 (CH$_2$=CH), 165.3 (C=O). MS; m/z 250.1 (MH$^+$,71%), 167 (100), 154 (35), 136 (23); HRMS: found 250.11835; C$_{12}$H$_{15}$N$_3$O$_3$ requires 249.1113. Elemental analysis: found: C, 57.88; H, 6.09; O, 16.92; C$_{12}$H$_{15}$N$_3$O$_3$ requires: C 57.82; H, 6.07; N, 16.86.

1b. Hexamethyltriamine trimethacrylate[4]:

Sulfuric acid (0.5 ml) was added drop wise to a solution of trioxane (4.50 g) and methacrylonitrile (10.05 g, inhibited with 50 ppm hydroquinone monomethyl ether). The temperature increased to 90° C. with the loss of some formaldehyde, and this temperature was maintained for a further 1 hour with some external heating required towards the end. Aqueous sodium hydroxide (0.40 g/ 10 ml) was then added drop wise. The oily product crystallized upon cooling and scratching of the flask surface to obtain a white solid from filtration. Recrystallization from ethanol produced (6.0 g, 41.27%) white crystals, m.p. 149–150° C., (lit[2]149.5–151° C.). $^1$H n.m.r. (CDCL$_3$): δ1.88 (9 H, s) CH$_3$; 5.12 (3 H, s) CH$_a$H$_b$=C; 5.31 (6 H, s) N—CH$_2$—N; 5.36 (3 H, s) CH$_a$H$_b$=C. $^{13}$C n.m.r. (CDCl$_3$); δ20 (CH$_3$); 57.5 (N—CH$_2$—N); 118.1 (CH$_2$=C); 139 (CH$_2$=C); 172 (C=O). MS: m/z 292.2 (MH$^+$, 69%), 195 (100), 152 (8), 120 (17); HRMS: found 292.16673 C$_{15}$H$_{21}$N$_3$O$_3$ requires 291.1583 . Elemental analysis found: C, 61.81; H, 7.39; N, 14.47; C$_{15}$H$_{21}$N$_3$O$_3$ requires C, 61.83; H, 7.27; N, 14.43.

EXAMPLE 2

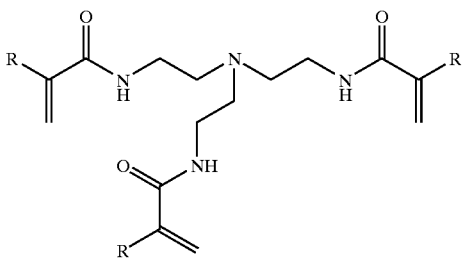

2a, R = H
2b, R = H

EXAMPLE 3

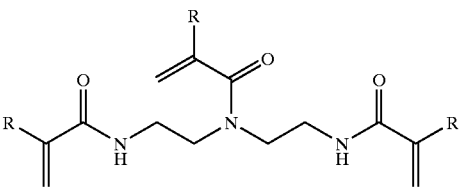

3a, R = H
3b, R = CH₃

2a. Triacryloyl-tris(2-aminoethyl)amine:

Tris(2-aminoethyl)amine (3.65 g, 0.025 moles) in dichloromethane (45 ml) was added drop wise over 2 hours to a solution of acryloyl chloride (6.78 g, 0.075 moles) in dichloromethane (55 ml) whilst stirring vigorously on an ice salt bath, maintaining the temperature between 0–5° C., in a three necked round bottom flask. The reaction mixture was then left to stir overnight at room temperature, where a white suspension was formed. The solid obtained from filtration was dissolved in water, neutralized with NaOH (aq) and extracted with ethyl acetate. A white solid was obtained and recrystallized from acetone to yield (1.164 g, 15.12%) white crystals., m.p. 118.5–120° C. $^1$H n.m.r. $\delta$(D$_2$O), 6.22 (3 H, dd, J9.9 Hz) CH=CH$_2$; 6.19 (3 H, dd, J 1.5 Hz) CH=CH$_a$H$_b$;576 (3 H, dd, J 1.5 Hz) CH=CH$_a$H$_b$3.37 (6 H, t, J 6.1 HzO N—CH$_2$—CH$_2$; 2.73 (6 H, t, J 6.1 Hz) N—CH$_2$—CH$_2$. $^{13}$C n.m.r. $\delta$(D$_2$O), 171.33 (C=O), 132.75 (CH=CH$_2$), 130.23 (CH=CH$_2$), 54.92 (N—CH$_2$—CH$_2$), 39.88 (N—CH$_2$—CH$_2$), MS; mz: 309.2 (MH$^+$, 1%), 224 (82), 195(9), 141(7),127(19), 98(100), 55(7). HRMS: found 309.19304; C$_{15}$H$_{24}$N$_4$O$_3$ requires 308.1848. I.R. (KBr) (cm$^{31\ 1}$): 3288, 3220; 1653, 1619, 1558, 1276. Elemental analysis: found: C, 58.27; H, 7.98; N, 18.14. C$_{15}$H$_{24}$N$_4$O$_3$ requires C, 58.42; H, 7.85; N, 18.17.

2b. Tri-methacryloyl-tris(2-aminoethyl)amine:

Tris(2-aminoethyl)amine (3.65 g, 0.025 moles) in dichloromethane (45 ml) was added drop wise over 2 hours to a solution of Methacryloyl chloride (7.84 g, 0.075 moles) in dichloromethane (55 ml), stirring vigorously at room temperature in a three-necked round bottom flask. The suspension formed was then left to stir overnight at room temperature and filtered. The white solid obtained was dissolved in water, neutralized with NaOH (aq) and extracted with ethyl acetate. The filtrate was then extracted with water, neutralized with NaOH (aq) and then extracted with ethyl acetate. The ethyl acetate layers were then combined and the solvent was rotary evaporated. The oily residue obtained was run through a silica gravity column using acetone as the elutant to obtain a yellow oil (3.24 g, 36.98%). $^1$H n.m.r. $\delta$(D$_2$O), 5.69, s, C=CH$_2$; 5.46, s, C=CH2; 1.91, s, CH3; 3.40, t, J 6.3 Hz, CH$_2$—CH$_2$); 130.23 (CH$_{2I=CH}$); 54.92 (N—CH$_2$—CH$_2$); 39.88 (N—CH$_2$—CH$_2$), MS: mz: 351(MH$^+$, 1%):, 265(9), 252(100), 180(8), 155(6), 141(18); HRMS: found: 351.23878; C$_{18}$H$_{30}$N$_4$O$_3$ requires 350.2318.

3a. Triacryloyl diethylene triamine

Diethylene triamine (2.06 g, 0.020 moles) in dichloromethane (45 ml) was added drop wise over 2 hours, to a solution of acryloyl chloride (5.43 g, 0.06 moles) in dichloromethane (55 ml), stirring vigorously at room temperature in a three necked round bottom flask. The resulting suspension was then left to stir for 24 hours at room temperature and then filtered. The solid obtained was dissolved in water, neutralized with NaOH(aq) and extracted with ethyl acetate. Similarly, the filtrate was extracted with water, neutralized with NaOH(aq) and extracted with ethyl acetate. The ethyl acetate fractions were combined and the solvent was rotary evaporated to leave behind a yellow oily residue which was run through a silica gravity column using acetone as the elutant to obtain a pure yellow oil (1.71 g, 16.12%). $^1$H n.m.r. $\delta$(D$_2$O)$\delta$6.69 (1 H, m) CH=CH$_a$H$_b$; 6.20(5 H, m) CH=CH$_a$H$_b$;5.76(3 H, m)CH=CH$_2$; 3.65(4 H, t, 5.8 Hz) NH—CH$_2$—CH$_2$;3.53(4 H, t, 5.7 Hz) NH—CH$_2$—$_{CH2}$ $^{13}$C n.m.r. (D$_2$O)$\delta$172.53, 171.74, 171.62(C=O); 132.68, 132.52, 131.64 (CH=CH$_2$); 130.51, 130.28, 130.00 (CH=CH$_2$); 49.98, 48.09 (N—CH$_2$—CH$_2$), 40.25, 39.81 (N—CH$_2$—CH$_2$). MS: mz: 266.1 (MH$^+$, 12%):, HRMS: found:266.15149; C$_{13}$H$_{19}$N$_3$O$_3$ requires 265.3083.

3b. Tri-methacryloyl diethylene triamine

Diethylene triamine (2.06 g, 0.020 moles) in dichloromethane (45 ml) was added drop wise over 2 hours to a solution of methacryloyl chloride (6.27 g, 0.06 moles) in dichloromethane (55 ml), stirring vigorously at room temperature in a three necked round bottom. The suspension formed was then left to stir overnight at room temperature, and then filtered. The white solid obtained was dissolved in water, neutralized with NaOH(aq) and extracted with ethyl acetate to obtain a pure yellow oil (0.09 g, 0.8%). The filtrate obtained was extracted with water, neutralized with NaOH (aq) and the water layer was extracted with ethyl acetate. The ethyl acetate was rotary evaporated and the yellow oily residue was put through a silica gravity column using acetone as the elutant to get a pure yellow oil. $^1$H n.m.r. (D$_2$O) $\delta$5.72(2H, d, J 17.5 Hz) C=CH$_2$; 5.49(2 H, d, 12.3 Hz) C=CH$_2$;5.27(2 H, d, 101.3) C=CH$_2$;3.64(4 H, quintet, J 5.7 Hz) NH—CH$_2$—CH$_2$3.53 (4 H, m) NH—CH$_2$—CH$_2$1.92(3 H, s) CH$_3$; 1.87 (6 H, s)CH$_3$; $^{13}$C n.m.r.(D$_2$O) $\delta$179.05, 174.67, 174.62 (C=O);142.27, 141.75, 141.53 (C); 124.51, 124.11, 119.74 (CH$_2$); 50.29, 45.79, 40.21, 39.59 (NH—CH$_2$—CH$_2$); 22.27, 20.47 (CH$_3$). MS: mz: 308.2(MH$^+$,100%), 242.1 (3), 272.2 (12), 186.2 (6),135 (10), 112.1 (29); HRMS: found: 308.19778; C$_{16}$H$_{25}$N$_3$O$_3$ requires: 307.3881. I.R. (KBr) (cm$^{-1}$) 3334, 1660, 1610, 1524, 1306.

EXAMPLE 4

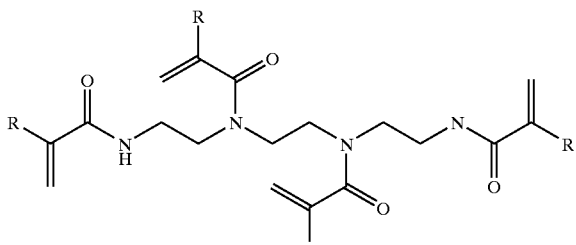

4a, R = H
4b, R = CH$_3$

4a. Tetra acryloyl triethylene tetramine

Triethylene tetramine (2.93 g, 0.02 moles) in dichloromethane (100 ml) was added drop wise over 6 hrs to a solution of acryloyl chloride (7.24 g, 0.08 moles) in dichloromethane (40 ml), stirring vigorously at room temperature. The reaction was stirred at room temperature overnight and the suspension was filtered. The filtrate was extracted with NaOH(aq). The water was rotary evaporated and the residue was washed with acetone and filtered. The acetone washings were concentrated down and the yellow oil remaining was put through a silica gravity chromatography column with acetone as the elutant. A yellow solid was obtained and recrystallized with cold diethyl ether to give white crystals, m.p. 107–109.5° C. $^1$H n.m.r (D$_2$O)) δ6.60(4 H, m) CH=CH$_2$;6.16 (6 H, m), CH=CH$_2$; 5.79(2 H, m), CH=CH$_2$;3.61 (6 H, m) N—CH$_2$—CH$_2$,3.52(6 H, m) N—CH$^2$—CH$_2$. $^{13}$C n.m.r (D$_2$)) δ172.52, 172.39, 171.78, 171.70 (C=O); 132.70, 132.55, 132.14, 131.74 (CH=CH$_2$), 130.52, 130.32, 129.93, 129.64 (CH=CH$_2$), 50.35, 49.82, 49.35, 48.31, 47.33, 46.05 (NH—CH$_2$—CH$_2$). MS: mz: 363.2 (MH$^+$, 100%), 291.2 (16), 238.1(6), 195.1 (74); HRMS: found:363.20204; C$_{18}$H$_{26}$N$_4$O$_4$ requires: 362, 4236Elemental analysis: found: C, 59.71; H, 7.22; N, 15.37; C$_{18}$H$_{26}$N$_4$O$_4$ requires C, 59.65; H, 7.23; N, 15.46. L.R. (KBr) (cm$^{-1}$): 3283, 3423, 1672, 1642, 1552, 1278.

4b. Tetra methacryloyl triethylene tetramine

Triethylene tetramine (2.93 g, 0.02 moles) in dichloromethane (100 ml) was added drop wise over 6 hrs to a solution of methacryloyl chloride (8.32 g, 0.08 moles) in dichloromethane (40 ml), stirring vigorously at room temperature. The reaction was continued stirring at room temperature overnight and the suspension formed was filtered. The filtrate was extracted with NaOH (aq). The water was rotary evaporated and the residue was washed with acetone and filtered. The acetone filtrate was concentrated down and put through a silica gravity chromatography column with acetone as the elutant to obtain a white solid. The solid is recrystallized from diethyl ether to give white crystals, m.p. 168–170° C. $^1$H n.m.r. (D$_2$O) δ, 5.71(19.7 Hz), 5.51 (7.8 Hz), 5.31(9.7 Hz), 5.06 (17.7 Hz), (8 H, d×4) C—CH$_2$; 3.61 (6 H, m) N—CH$_2$—CH$_2$; 3.48(6 H, m) N—CH$_2$—CH$_2$; 1.96(4.1 Hz); 1.93(5.8 Hz); 1.91(6.0 Hz); 1.88(4.5 Hz), (12 H, d×4) CH$_3$; $^{13}$C n.m.r. (D$_2$O), δ 178.76, 178.70, 174.71, 174.61 (C=O); 142.19, 142.0, 141.71, 141.56 (C=CH$_2$), 124.52, 124.19, 120.06, 119.60 (C=CH$_2$); 22.30, 22.20, 20.48; (CH$_3$), 50.33, 49.22, 46.45, 44.00, 40.22, 39.49 (N—CH$_2$—CH$_2$). MS: mz: 419.3 (MH$^+$, 100%), 391.3(4), 266.2(10), 223.1(42); HRMS: found: 419.26695 C$_{22}$H$_{34}$N$_4$O$_4$ requires 418.5299. Elemental analysis: found: C, 62.97; H, 8.09; N, 13.31; C$_{22}$H$_{34}$N$_4$O$_4$ requires C, 63.13; H, 8.19; N, 13.39. I.R. (KBr) (CM$^{-1}$) 3353, 1665, 1650, 1530, 1279.

EXAMPLE 5

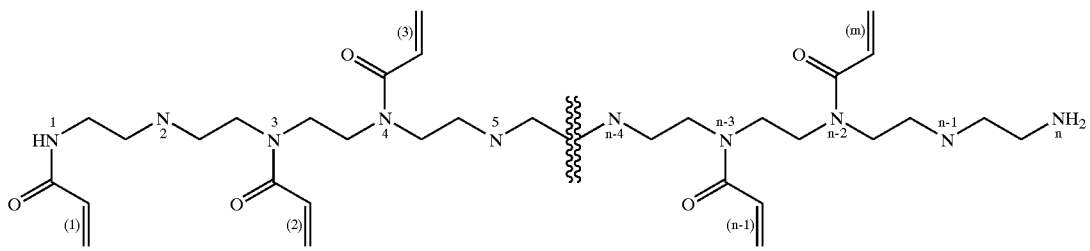

Polyethylenimine Acrylates

Method A:

Polyethylenimine (0.01 moles) was dissolved in acetonitrile (100 ml) in a 250 ml round bottom flask and stirred vigorously at room temperature a under a flow of nitrogen. The acid chloride (acryloyl or methacryloyl chloride) in acetonitrile (50 ml) was then added drop wise over two hours. The suspension formed was left to stir for a further 24 hours at room temperature before it was filtered. The filtrate was then evaporated, and the oil residue was dissolved in water, neutralized with NaOH (aq) and then extracted with ethyl acetate. The ethyl acetate was concentrated down and subjected to a series of silica gravity chromatography columns with the elutants acetone and ethyl acetate.

Example of Method A

| PEI | PEI (moles) | Methacryloyl chloride | Product |
| --- | --- | --- | --- |
| Linear (Mn 423) | 4.23 g, 0.01 moles | 4.18 g, 0.04 moles | LPEI-4M-9-8 |

LPEI-4M-9-8

Yellow oil was obtained with the following characteristics. MS: esi: 951.6 (MH$^+$, 6%), 840.4 (8), 752.2 (25), 641.2 (100), 530.1 (63), 419.1 (8), 308.1 (4), 1H n.m.r. (D$_2$O) δ 5.32 (16 H, m) C=CH$_2$; 3.59 (36 H, m) N—CH$_2$—CH$_2$; 1.92 (24 H, m) CH$_3$.

Method B:

Polyethylenimine (0.01 moles) was dissolved in dichloromethane (1.50 ml) and stirred vigorously under nitrogen at room temperature. To this was added crushed NaOH pellets that remained as a suspension in solution, on an equal mole ratio to the acid chloride. A solution of an acid chloride in dichloromethane, (50 ml) was immediately added to the solution drop wise over two hours. The reaction was then left to stir for a further 24 hours at room temperature before being filtered. The filtrate was concentrated down and the oil was subjected to a series of silica gravity chromatography column using the elutants dichloromethane and methanol to obtain the desired product.

Example of Method B

| PEI | Reaction | Methacryloyl chloride | NaOH | Product |
|---|---|---|---|---|
| Linear, 423 | 4.23 g, 0.01 moles | 12.54 g, 0.12 moles | 4.80 g, 0.12 moles | LPEI-4M-10-8 |

LPEI-4M-10-8

A yellow oil was obtained with the following characteristics, MS: esi: 992.81 ($MH^+$, 1%), 753.7 (8), 684.6 (25), 573.5 (100), 531.5 (82), 462.7 (23), 419.4 (19), 351.4 (4). $^1$H n.m.r. ($D_2O$) δ 5.34 (16 H, m) C=$CH_2$; 3.47 (40H, m) N—$CH_2$—$CH_2$; 1.92 (24 H, m) $CH_3$.

General Procedure for Making Polyacrylamide Gels

A general procedure for preparing stock solutions of acrylamide and the crosslinker of interest, and the preparation of SDS gels used for SDS-PAGE were described below. SDS-PAGE gels were performed and prepared under the discontinuous conditions of Laemmli[4] Some general features are:

- To ensure that the degree of crosslinking is equivalent for all crosslinking agents with equivalent functionality (number of polymerizable groups), all substitutions are calculated on a mole; mole basis rather than a weight basis.
- When the functionality (number of polymerizable groups) varies between the crosslinkers, the substitutions are calculated on the number of double bond equivalent basis.
- The term % T refers to the concentration of total monomer (w/v), and % C refers to the concentration of the crosslinking monomer (w/w) as a portion of % T. Depending on the combination of % T to % C required, the concentration of acrylamide (% T) remains constant with the stock solution usually 30% T. Whilst the concentration of the crosslinker (% C) is varied accordingly, with the stock solution usually being between 2% and 15%C.
- All new gel systems were initially calculated so that they correspond to the standard acrylamide/BIS (N,N'-Methylenebisacrylamide) system. Therefore, the calculations for a 30% T 3% C stock monomer solution will contain 14.55 g of acrylamide per 50 ml solution and the amount of crosslinker added is shown in table 1 below.

EXAMPLE 6

Preparation of the Stock Monomer Solutions

Dissolving 14.55 g acrylamide with the appropriate amount of crosslinker (shown in table 1 below) in a 50 ml volumetric flask with distilled water makes up a 30%T 3% C stock solution. The solution is filtered through a Whatman No. 1 filer paper and can be stored at 4° C. prior to use for up to two months.

TABLE 1

| Crosslinker | Crosslinker (g) (3% C) | Acrylamide (g) (30% T) |
|---|---|---|
| BIS | 0.450 | 14.55 |
| (1a) | 0.485 | 14.55 |
| (1b) | 0.567 | 14.55 |
| (2a) | 0.600 | 14.55 |
| (2b) | 0.682 | 14.55 |
| (3a) | 0.516 | 14.55 |
| (3b) | 0.598 | 14.55 |
| (4a) | 0.529 | 14.55 |
| (4b) | 0.611 | 14.55 |

EXAMPLE 7

Preparation of the Polyacrylamide Gels

The polyacrylamide gel is generally prepared by mixing the required amounts of monomer stock solution, distilled water and 1.5 M Tris-HCl buffer (pH 8.8). The 1.5 M Tris-HCl buffer (pH 8.8) used in gels was made by dissolving Tris(hydroxymethyl)amino methane (TRIS, 27.23 g) in distilled water (80 ml). 6 N HCl is added until the pH reaches 8.8 and the volume is adjusted to 150 ml with distilled water and stored at 4° C. To vary the concentration of the gel, variable amounts of water and monomer stock solution are used. The gel solution once prepared was degassed by vacuum aspiration at room temperature for 40 minutes. It was then purged with nitrogen whilst the initiator system is added. There were two initiator methods used to polymerize the gel solutions.

Method A: Redox initiation

The initiator system was composed of freshly made up 10% (w/v) of ammonium persulphate (APS) and 10% (w/v) of tetramethylethylenediamine (TEMED) with the ratio of APS to TEMED constant at 1:1. The gel solution is quickly and carefully injected and cast between two glass cassettes (8×8 cm, 1 cm apart) purged with nitrogen. The solution is then left purging with nitrogen for a further 120 minutes to polymerize.

Method B: Photopolymerization

Alternatively, the gels may be polymerized via photopolymerization. Aqueous solutions of the photoinitiators RBF (20 mM), STS (250 mM) AND DPIC (10 mM) or TEMED 10% (w/v) (1.0 μl) were added to each degassed gel solution purging with nitrogen. The gel solution is quickly and carefully injected and cast between two glass cassettes (8×8 cm, 1 cm apart) and polymerized by illuminating with a 500 W halogen light for twenty minutes at a distance of 20 cm away. The gels were then left at room temperature for at least 2 hours.

EXAMPLE 8

Polymerization Conversion

Method A:

The degree of co-polymerization was measured for each polyacrylamide gel made as shown above. The gel was removed from the glass cassettes, weighted, crushed in a beaker and washed with methanol three times to dissolve all the unreacted monomers. The methanol washings were then combined filtered and made up in a 50 ml volumetric flask with methanol. A 5.0 μl sample of this solution was injected and analyzed using a HPLC. A peak is usually obtained representing the unreacted double bonds present in the methanol solution, and then measured against an acrylamide standard to calculate the amount of unreacted monomers present.

Method B:

The methanol washings were obtained as above and then rotary evaporated to remove the methanol. The resulting residue was dissolve in deuterated water and 5.0 μg of hydroquinone (as the standard) and measured using $^1$H NMR. Any peaks obtained representing the unreacted double bonds were integrated and calculated against the hydroquinone standard.

General Procedures for Analysis of Polyacrylamide Gels with Crosslinkers of Invention Compared with Standard BIS-Acrylamide Gels

EXAMPLE 9

SDS-PAGE

The migration pattern of a broad range molecular weight sample of protein or DNA markers, separated by SDS-PAGE, using polyacrylamide gels made with the new crosslinkers were compared and examined. All the polyacrylamide gels were made as above. A stacking gel with a concentration of 5% T 3% C was similarly made using the crosslinker BIS. The stacking solution is syringed onto the top of the polyacrylamide gel in the cassettes that contain a plastic mould for the formation of loading wells for the protein samples. The solution is left to polymerize under nitrogen for 60 minutes before being used for SDS-PAGE or stored at 4° C. for 24 hours. Electrophoresis was performed at a constant voltage of 150 V for one hour using a constant power supply, a Gradipore Limited micrograd vertical electrophoresis unit and a TRIS electrophoresis running buffer. The electrophoresis running buffer is made by dissolving TRIS (9 g), Sodium dodecyl sulphate (SDS, 43.2 g) and glycine in 100 ml of distilled water in a volumetric flask. Before use, this solution was diluted 1:5 with distilled water. A 10 μl peptide or DNA sample was microsyringed into the sample wells embedded in the stacking gel and separated by electrophoresis. The gels were then stained with coomassie blue R-250 or silver stained to observe the migration pattern. The relative mobility (Rf) which is the distance migrated by the protein or DNA divided by the distance travelled by the dye front is measured and plotted against the log of the molecular weight of each protein or DNA fraction.

EXAMPLE 10

Gelation Tests

Gelation tests were done to observe the nature of the polymerization reaction and the amount of time required for the monomer solution to gel. A monomer solution was prepared as described above but cast into small glass vials that had been purged with nitrogen and contained a thin temperature probe to record the temperature during the exothermic free radical polymerization. As soon as the monomer solution was prepared the glass vials were capped and the temperature probes began taking readings every 30 seconds for 2 hours. The temperature data obtained was then plotted against time to measure the gel times, Tmax and the polymerization rate.

EXAMPLE 11

Water Swelling

Water swelling tests were made to investigate the porosity of gels via the amount of water absorbed by the gel. A 3×3 cm piece of the polyacrylamide gel (made as described above) containing the new crosslinker, was cut, weighted and dried in a 60° C. oven for 24 hours. The dry gel was then weighed down and immersed in 100 ml of distilled water maintained at 20° C. in an insulated plastic container. Every 10 minutes for 2 hours the gel was removed from the water, patted with filter paper to remove excess surface water and weighted. The gels were then held left to soak in the water overnight to become saturated before being re weighted. The amount of water uptake was calculated as the ratio of the weight of the water gained between the dry gel and the swollen gel after a specific time, over the weight of the dry gel. This ratio was plotted against time to measure the degree of swelling of each gel.

EXAMPLE 12

Differential Scanning Calorimetry (DSC)

The DSC was also used to investigate the porosity of the gels. The polyacrylamide gels were made as shown above, and 9–12 mg of the gel was cut and placed in a non-hermetic pan. The sample was cooled to −30° C. so that the water in the gel solidifies. It was then heated at 1° C./minute to 150° C., so the solid state water would melt at about 0° C. and boil at about 100° C. An endothermic peak for the phase transitions of the water is observed. Part of the water contained in the gel was bound on the surface of the polymer network and this so-called bound water is different from pure water. These water molecules were considered to be mixed with impurity (the impurity being the polymer network). Therefore, causing a lower and different melting temperature than pure water. Non bound water in the gel was found to melt at a higher temperature than 0° C. These two water peaks are due to bound and non bound water in the gel and will provide information about the gel network.

EXAMPLE 13

Scanning Electrons Microscopy (SEM)

SEM was used to observe the morphology of the gel polymer network. Most techniques used to investigate the pore sizes and pore size distribution of materials require the porogen to be removed from within the pores. Polyacrylamide gels are hydrogels and have water inside the pores. When the water is removed from the pores the gel shrinks due to the phase transitions and causes the network to collapse. This inhibits the accuracy and availability of some techniques. Cryogenic SEM freeze dries the gels and sublimes the water at a temperature which is low enough to remove the surface water but maintains the polymer structure. Using the polyacrylamide gels containing the new crosslinkers as made above a small 5×5 mm piece of the gel is cut and cryogenically fractured in liquid nitrogen. It is then mounted vertically on a SEM stub with a non conductive glue before subliming the water at −95° C. for 90 minutes. The sample was then cooled to −198° C., coated with platinum using argon gas and plasma for 2 minutes. Images of the fractured polymer were then taken at various magnifications.

EXAMPLE 14

Electrophoretic Separation Analysis

Samples of known molecular weight and size were run through a Gradiflow™ Babyflow™BF200 unit to investigate the relative pore size formed in polyacrylamide networks by varying the crosslinker and/or the concentration. 30% T 3% C acrylamide solutions used above to make gels were polymerized into thin membranes with non woven PET sheet as the supporting substrate which were used as the electrophoretic separation membrane. The protein standards used were placed in a buffer solution and run by a current from the upstream section of the unit above the membrane. Proteins smaller than the pores of the membrane will pass through the membrane into the down stream section of the unit. The larger proteins will be recycled back into the upstream section. 10 μl samples from both the upstream and down stream sections of the unit are taken every 10 minutes for 30 minutes and detected using SDS-PAGE. The migration patterned should indicate what sized samples passed through the membrane. Therefore, the biggest pore size for a particular membrane is measured.

Gel Characterisation results

FIG. 1 is a diagram of eight crosslinkers in accordance with the present invention and their abbreviations that were evaluated in polyacrylamide gels.

EXAMPLE 15

SDS-PAGE

The migration pattern observed for a protein molecular weight marker separated by electrophoresis, allows us to indirectly investigate the porosity of a polyacrylamide gel. Therefore, polyacrylamide gels crosslinked with novel polyfunctional and multifunctional crosslinkers were made and analyzed using SDS-PAGE. Rf (retardation factor) is the distance migrated by the protein divided by the distance travelled by the dye front. The % difference is the [Rf (crossliner) minus Rf (BIS) divided by Rf (BIS)] ×100. The % difference or the Rf can then be plotted against the log of the molecular weight of each protein fraction.

FIGS. 2a and 2b are graphs of the Rf values plotted against the log of the molecular weight of the respective protein fractions obtained for eight of the new polyacrylamide gels compared with BIS. All the newly crosslinked gels showed different protein migration patterns to BIS and each other.

FIGS. 3–5 are graphical representations of the % difference a particular molecular weight fraction is separated on each newly crosslinked gel by electrophoresis compared to BIS crosslinked gels.

FIG. 3 shows the % difference of four of the new crosslinkers. The crosslinkers vary in the skeletal structure and the number of double bonds. However, all the double bonds have essentially the same reactivity with BIS. Most of the newly crosslinked gels appeared to show greater separation for the larger molecular weight fractions (>116,500 Dalton). However, the amount of increased separation was less significant for the smaller molecular weight fractions. The largest different was observed between the crosslinkers 3a and 4a. 4a is longer than 3a by one extra ethylene unit and double bond, but appears to have a greater separation for the entire molecular weight region tested, which suggests larger pore sizes and a greater pore size distribution.

FIG. 4 compares the % difference of two sets of crosslinkers, 2a, with 2b and 4a with 4b. The crosslinker sets have the same skeletal backbone and number of double bonds, but the reactivity of the double bonds is different. 2a and 4a are acrylates, but 2b and 4b are more reactive methacrylates. Both 2b and 4b show a slightly greater separation pattern than 2a and 4a respectively for the entire range of molecular weight markers tested. This suggests that the greater reactivity of the methacrylate double bonds, which are incorporated into the 3d-polymer network quicker, must do so in a way that results in slightly bigger pore size.

Polyacrylamide gels containing two different crosslinkers in the one gel were also made. FIG. 5 above shows the % difference observed between gels containing the crosslinker 1a, 1b or both 1a and 1b (in a 1:1 ratio with a total 10% T 3% C concentration). Surprisingly the gel containing both 1a and 1b appear to have an increased protein separation for the middle to lower molecular weight region compared to 1a and 1b.

To better understand the role of the crosslinker and the observations made during electrophoresis, further tests were made to investigate the porosity of the gel. The % conversion between acrylamide and the crosslinker monomers into a 3d-polymer network were measured. Most of the crosslinkers showed a very high conversion (>99%).

EXAMPLE 16

Water Swelling

The amount of water absorbed by the polyacrylamide gel was calculated, as the Ratio of the weight of the wet gel minus the weight of the dry gel divided by the weight of the dry gel. This ratio was plotted against time and shown in FIG. 6. All the gels tested swelled in water gradually, and even after saturation with water were handled without breaking. From FIG. 6 it can be seen that the gels that have the greatest swelling difference to BIS appear to also have the greatest protein separation difference to BIS during SDS-PAGE. However, it is not imperative that a correlation exists for this invention between the results obtained from each analytical procedure used.

EXAMPLE 17

DSC

DSC analysis supports the results and patterns obtained from the water swelling tests observed above. The endothermic peak for the melting of the solid state bound water and free water is observed as one broad peak. As seen from the data obtained in Table 2 below, generally all the gels exhibit a lower melting temperature than that obtained for pure water due to the influence of the bound water. The gels that experience the largest temperature deviation from BIS appear to also exhibit the greatest protein separation.

TABLE 2

| Samples | Water melting temperature |
| --- | --- |
| water | −0.32 |
| gels with 3b | −1.73 |
| gels with BIS | −1.63 |
| gels with 1a | −1.60 |
| gels with 1b | −1.46 |
| gels with 3a | −1.43 |
| gels with 2b | −1.10 |
| gels with 2a | −1.09 |
| gels with LPEI-4M-9-8 | −1.01 |
| gels with 4b | −0.95 |
| gels with a mixture of 1a:1b (1:1) | −0.52 |

EXAMPLE 18

Electrophoretic Separation Analysis using Gradiflow™ System

FIG. 7 shows the separation and migration pattern of the protein molecular weight marker samples taken from the Gradiflow™ unit after electrophoresis and analysis by SDS- PAGE. The membranes used in the Gradiflow unit for protein separation were made from polyacrylamide with a concentration of 30% T 10% C and crosslinked with BIS or 1a. It is clearly seen that the membrane crosslinked with 1a has slightly bigger pore sizes because one of the larger proteins (67 dKa) was able to pass from the upstream to the downstream sections using the 1a membrane. However, the same protein fraction was contained in the upstream section when the BIS membrane was used.

To understand the observations made above, SEM and gelation tests were made to investigate the morphology of the 3d-polymer network.

EXAMPLE 19

SEM

FIG. 8 shows the picture taken using cryogenic SEM for polyacrylamide gels crosslinked with BIS, 1a, or 1b. The pictures clearly show the pore distribution and the morphology of the polymer network. The polyacrylamide gel containing crosslinker 1b appears to have an area concentrated with small pores in between areas containing larger pores. Such morphology supports the theory that the more reactive methacrylate double bonds of the crosslinker 1b, will react and polymerize faster forming these highly dense areas which will begin to react and incorporate the acrylate double bonds into the polymer network later. The polyacrylamide gel crosslinked with 1a appears to contain an evenly broad pore size distribution. In comparison, BIS contains narrow and evenly distributed pores. This suggests that the cyclic and branched structure of 1a and 1b direct the growth of the polymer in all directions with longer chains resulting in a different polymer network.

EXAMPLE 20

Gelation Tests

FIG. 9 is a graphical representation of the temperature changes occurring over time during the free radial polymerization of a polyacrylamide gel using the crosslinkers BIS, 1a, 1b and a mixture of 1a with 1b (1:1). The time the temperature begins to increase is called the gel time. The gels containing 1a, 1b and their mixture gel quicker than BIS. The rate of the reaction appears to be dictated by the reactivity of the double bonds, 1a and BIS which are acrylates have a steeper slop than 1b which is a methacrylate.

REFERENCES

1. O'Connell, P. B. H; Brady, C. J. *Anal. Biochem.*, 1976, 16, 63.
2. Hochstrasser, D. F.; Patchorhik, A; Merril, C. R. *Anal. Biochem.*, 1978, 173, 412.
3. Emmons, W. D.; Rolewicz, H. A.; Cannon, W. N.; Ros. R. W., *J. Am. Chem Soc.* 1952, 74, 5524
4. Laemmli, U. K, *Nature,* 1970, 22 7, 680–685

It will be appreciated by persons skilled in the art that numerous variations and/or modifications may be made to the invention as shown in the specific embodiments without departing from the spirit or scope of the invention as broadly described. For example, although the present invention has been described in relation to polymer gels formed from acrylamide monomers it will be readily seen that the invention has application to polymer gels formed from other monomers conventionally used in bio-compatible applications such as prosthetic devices and optical and eye lenses.

The present embodiments are, therefore, to be considered in all respects as illustrative and not restrictive.

What is claimed is:

1. A crosslinked polymer gel formed from at least one monomer and a combination of crosslinkers, the crosslinkers including at least one crosslinker having at least three crosslinkable functional groups and at least one crosslinker having two crosslinkable functional groups, wherein at least one of the crosslinkable functional groups is selected from the group $CH_2=C(R)—O—$ and $CH_2=C(R)—S—$, where R is H or optionally substituted alkyl.

2. The crosslinked polymer gel according to claim 1 wherein the crosslinker having at least three crosslinkable functional groups is a compound of formula II

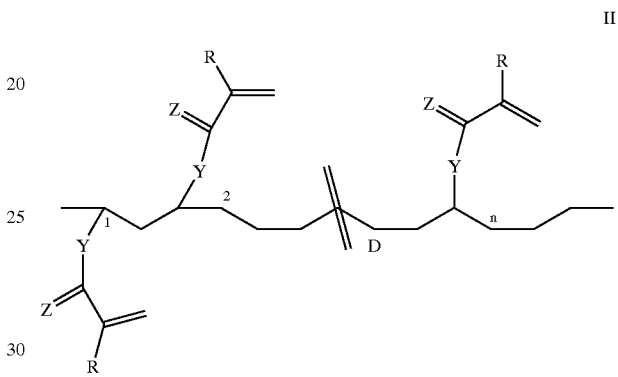

wherein

D represents a backbone chain of the crosslinker which is connected with at least three functional groups —Y—CZC(R)=$CH_2$ which functional groups are the same or different;

Y in each functional group is the same or different and selected from the group consisting of a single bond, N, O, or S; and Z in each functional group is the same or different and selected from O or S; and R in each functional group is the same or different and selected from hydrogen or optionally substituted alkyl.

3. The crosslinked polymer according to claim 2 wherein backbone D is selected from the group consisting of a monomer, an oligomer, and a polymer.

4. The crosslinked polymer gel according to claim 3 wherein backbone D is an alkyleneimine oligomer or polymer.

5. The crosslinked polymer gel according to claim 3 wherein backbone D is an alkyleneoxide oligomer or polymer.

6. The crosslinked polymer gel according to claim 2 wherein the backbone D is an aliphatic chain which is linear or branched, saturated or unsaturated, optionally substituted or optionally interrupted by one or more heteroatoms O, S, N, or one or more aromatic, saturated or unsaturated heterocyclic or carbocyclic radicals.

7. The crosslinked polymer gel according to claim 2 wherein the crosslinker of Formula II has the formula:

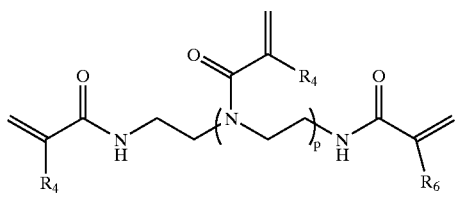

wherein $R_4$, $R_5$, and $R_6$, which are the same or different, are selected from H or alkyl and p is 1 to about 6.

8. The crosslinked polymer gel according to claim 2 wherein the crosslinker of Formula II is selected from the group consisting of trimethacyloyldiethylenetriamine, triacryloyl-tris(2-aminoethyl)amine, trimethacryloyl-tris(2-aminoethyl)amine, tetraalcryloyl triethylene tetramine, tetramethacryloyl triethylene tetramine and mixtures of two or more thereof.

9. The crosslinked polymer gel according to claim 2 wherein the crosslinker of Formula II has the formula:

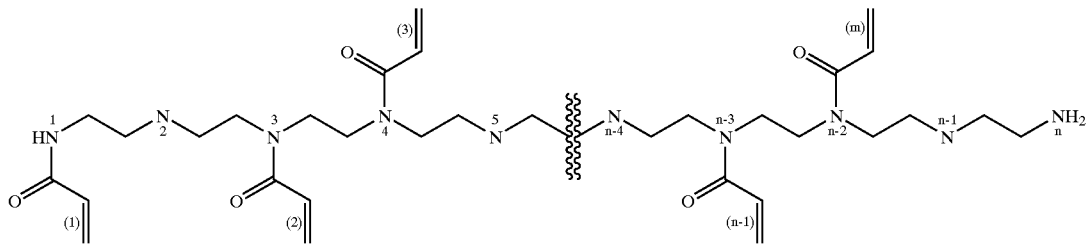

wherein n represents the number of repeating unit of polyethylene iminie backbone and m represents the number of acryloyl or methacryloyl groups substituted on the backbone wherein m and n are at least 3.

10. The crosslinked polymer gel according to claim 2 wherein the polymer gel is formed from at least one monomer and at least two crosslinkers having at least three crosslinkable functional groups $CZCR=CH_2$ wherein each crosslinker has functional groups from that of the other crosslinkers.

11. The crosslinked polymer gel according to claim 10 wherein at least one monomer is selected from the group consisting of acrylamide, N, N-dimethylacrylamide, methacrylamide, methyloylacrylamide, propylacrylamide, dipropyl acrylamide, isopropyl acrylamide, diisopropyl acrylamide, lactyl acrylamide, methoxyacrylamide and mixtures thereof.

12. The crosslinked polymer gel according to claim 1 wherein at least one monomer is of the formula $H_2C=CR_5—CO—NR_3R_4$ wherein $R_3$, $R_4$ and $R_5$ are each independently H or optionally substituted alkyl.

13. The crosslinked polymer gel according to claim 12 wherein at least one monomer is selected from the group consisting of acrylamide, N,N-dimethylacrylamide, methacrylamide, N-methyloylacrylamide, methyloylacrylamide, propylacrylamide, dipropyl acrylamide, isopropyl acrylamide, diisopropyl acrylamide, lactyl acrylamide, methoxyacrylamide and mixtures thereon.

14. The crosslinked polymer gel according to claim 1 wherein the polymer gel is formed from at least one monomer and at least two crosslinkers having at least three crosslinkable functional groups —$CZCR=CH_2$ wherein each crosslinker has different functional groups from that of the other crosslinker(s).

15. An electrophoretic medium containing a crosslinked polymer gel formed from at least one monomer and at least one crosslinker having at least three crosslinkable functional groups wherein at least one of the crosslinkable functional groups is $CH_2=C(R)—CO—$, where R is H or optionally substituted alkyl, wherein the gel has a porosity gradient or a composition gradient.

16. The electrophoretic membrane according to claim 15, wherein the crosslinked polymer gel is formed on a porous substrate.

17. A method for preparing a polymer gel having at least one preselected property selected from the group consisting of pore size range, pore size distribution, resistance to hydrolysis in alkaline media, clarity of gel and reduced background after silver staining, the method including combining at least one monomer with a crosslinker of Formula II below, optionally with at least one other crosslinker, optionally in the presence of an initiator, and subjecting at least one monomer and at least one crosslinker of Formula II to polymerization and crosslinking, wherein the nature or amount of the crosslinker of Formula II is selected to produce a gel having said at least one preselected property, Formula II:

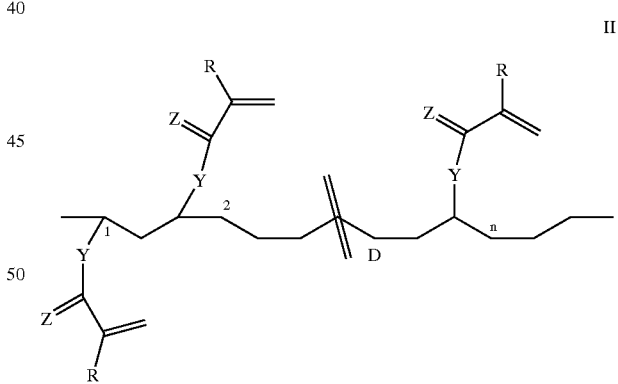

wherein
D represents a backbone chain of the crosslinker which is connected with at least three functional groups —Y—$CZC(R)=CH_2$ which functional groups are the same of different;
Y in each functional group is the same or different and selected from the group consisting of a single bond, N, O, or S; and
Z in each functional group is the same or different and selected from O or S; and
R in each functional group is the same or different and selected from hydrogen or optionally substituted alkyl.

18. The method according to claim 17 wherein at least one monomer is of the Formula $H_2C=CR_5—CO—NR_3R_4$ where $R_3$, $R_4$ and $R_5$ are each independently H or optionally substituted alkyl.

19. The method according to claim 18 wherein at least one monomer is selected from the group consisting of acrylamide, N,N-dimethylacrylamide, methacrylamide, methyloylacrylamide, propylacrylamide, dipropyl acrylamide, isopropyl acrylamide, diisopropyl acrylamide, lactyl acrylamide, methoxyacrylamide and mixtures thereof.

20. A compound of Formula II

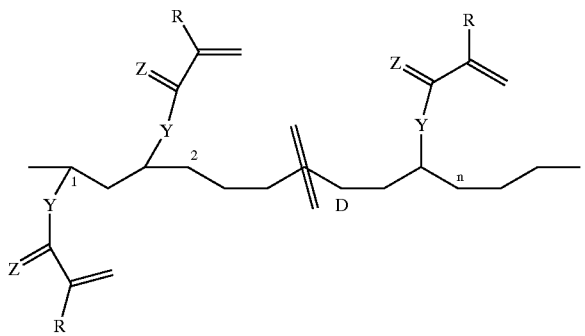

II wherein

D represents a backbone chain of the crosslinker which is connected with at least three functional groups —Y—CZC(R)=CH$_2$ which functional groups are the same or different;

Y in each functional group is the same or different and selected from the group consisting of a single bond, N, O or S;

Z in each functional group may is the same or different and selected from O or S; and R in each functional group is the same or different and selected from hydrogen or optionally substituted alkyl.

21. The compound according to claim 20 wherein backbone D is a monomer, an oligomer or a polymer.

22. The compound according to claim 20 wherein backbone D is an aliphatic chain which is linear or branched, optionally substituted, saturated or unsaturated, optionally interrupted by one or more heteroatoms O, S, N, or one or more aromatic, saturated or unsaturated heterocyclic or carbocyclic radicals.

23. The compound according to claim 22 wherein the compound has the formula:

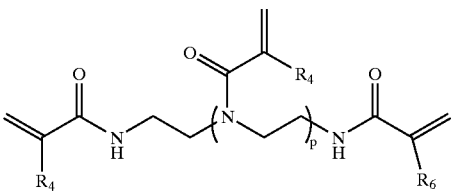

wherein $R_3$, $R_4$ and $R_5$, which may be the same or different, are selected from H or alkyl and p is 1 to about 6.

24. The compound according to claim 20 formed from at least one monomer selected from the group consisting of trimethacyloyldiethylenetriamine, triacryloyl-tris(2-aminoethyl)amine, trimethacryloyl-tris(2-aminoethyl) amine, tetraalcryloyl triethylene tetramine and tetramethacryloyl triethylene tetramine.

25. The compound according to claim 20 wherein backbone D is an alkyleneimine oligomer or polymer.

26. The compound according to claim 25 wherein the compound has the formula:

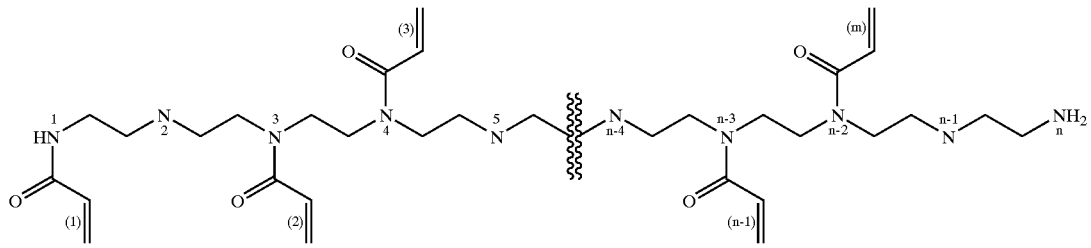

wherein n represents the number of repeating unit of the polyethylene imine backbone and m represents the number of acryloyl or methacryloyl groups substituted on the backbone, m being at least 3.

27. The compound according to claim 20 wherein backbone D is an alkyleneoxide oligomer or polymer.

28. A crosslinked polymer gel formed from at least one crosslinker and optionally at least one monomer, wherein the at least one crosslinker has at least three functional groups $CH_2=C(R)—CO—$, wherein R is H or $CH_3$, wherein at least one functional group is attached to a nitrogen and at least one other functional group is attached to a heteroatom other than nitrogen.

29. A crosslinked polymer gel formed from a mixture of crosslinkers and optionally at least one monomer, wherein the mixture of crosslinkers comprises (a) at least one crosslinker having at least three functional groups $CH_2=CH—CO—$ each attached to a nitrogen and (b) at least one crosslinker having at least three functional groups $CH_2=C(CH_3)—CO—$ each attached to a nitrogen.

30. A crosslinked polymer gel formed from a mixture of crosslinkers and optionally at least one monomer, wherein the mixture of crosslinkers comprises (a) at least one crosslinker having at least three functional groups $CH_2=CH—CO—$, wherein at least one functional group $CH_2=CH—CO—$ is attached to a nitrogen and at least one other functional group $CH_2=CH—CO—$ is attached to a heteroatom other than nitrogen and (b) at least one crosslinker having at least three functional groups $CH_2=C(CH_3)-CO-$, wherein at least one of functional groups $CH_2=C(CH_3)-CO-$ is attached to a nitrogen and at least one other functional group $CH_2=C(CH_3)-CO-$ is attached to a heteroatom other than nitrogen.

31. A crosslinked polymer gel formed from a mixture of crosslinkers and optionally at least one monomer, wherein the mixture of crosslinkers comprises (a) at least one crosslinker having at least three functional groups $CH_2=CH-CO-$, wherein each functional group $CH_2=CH-CO-$ is attached to a nitrogen and (b) at least one crosslinker having at least three functional groups $CH_2=C(CH_3)-CO-$, wherein at least one of functional groups $CH_2=C(CH_3)-CO-$ is attached to a nitrogen and at least one other functional group $CH_2=C(CH_3)-CO-$ is attached to a heteroatom other than nitrogen.

32. A crosslinked polymer gel formed from a mixture of crosslinkers and optionally at least one monomer, wherein the mixture of crosslinkers comprises (a) at least one crosslinker having at least three functional groups $CH_2=CH-CO-$, wherein at least one functional group $CH_2=CH-CO-$ is attached to a nitrogen and at least one other functional group $CH_2=CH-CO-$ is attached to a heteroatom other than nitrogen and (b) at least one crosslinker having at least three functional groups $CH_2=C(CH_3)-CO-$, wherein each functional groups $CH_2=C(CH_3)-CO-$ is attached to a nitrogen.

33. The crosslinked polymer composition according to any one of claims 28, 30, 31 and 32 wherein the heteroatom other than nitrogen is oxygen.

34. The crosslinked polymer according to claim 33 wherein the polymer is formed from the at least one crosslinker and at least one monomer containing at least two functional groups.

35. The crosslinked polymer gel according to claim 34 wherein at least one monomer containing at least two functional groups is of the formula $H_2C=CR_5-CO-NR_3R_4$ where $R_3$, $R_4$ and $R_5$ are each independently H or optionally substituted alkyl.

* * * * *